(12) United States Patent
Wandinger-Ness et al.

(10) Patent No.: US 12,123,881 B2
(45) Date of Patent: Oct. 22, 2024

(54) Rap1-GTP, Rac1-GTP and FMS-LIKE TYROSINE KINASE 3 LIGAND (FLT3-L) AS BIOMARKERS FOR EARLY DETECTION OF SEPSIS

(71) Applicant: UNM Rainforest Innovations, Albuquerque, NM (US)

(72) Inventors: Angela Wandinger-Ness, Albuquerque, NM (US); Tione Buranda, Albuquerque, NM (US); Peter Simons, Albuquerque, NM (US); Stephen Young, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 1007 days.

(21) Appl. No.: 17/048,941

(22) PCT Filed: Apr. 18, 2019

(86) PCT No.: PCT/US2019/028165
§ 371 (c)(1),
(2) Date: Oct. 19, 2020

(87) PCT Pub. No.: WO2019/204634
PCT Pub. Date: Oct. 24, 2019

(65) Prior Publication Data
US 2021/0231683 A1    Jul. 29, 2021

Related U.S. Application Data

(60) Provisional application No. 62/660,635, filed on Apr. 20, 2018.

(51) Int. Cl.
| | | |
|---|---|---|
| *G01N 33/68* | (2006.01) | |
| *G01N 15/14* | (2024.01) | |
| *G01N 33/563* | (2006.01) | |
| *G01N 33/58* | (2006.01) | |

(52) U.S. Cl.
CPC ......... *G01N 33/6893* (2013.01); *G01N 15/14* (2013.01); *G01N 33/563* (2013.01); *G01N 33/588* (2013.01); *G01N 2800/26* (2013.01); *G01N 2800/50* (2013.01)

(58) Field of Classification Search
CPC .. G01N 33/6893; G01N 15/14; G01N 33/563; G01N 33/588; G01N 2800/26; G01N 2800/50
See application file for complete search history.

(56) References Cited

U.S. PATENT DOCUMENTS

| | | | |
|---|---|---|---|
| 6,291,661 B1* | 9/2001 | Graddis | C07K 14/52 435/69.7 |
| 10,261,084 B1 | 4/2019 | Buranda et al. | |
| 10,962,541 B2 | 3/2021 | Buranda et al. | |
| 2002/0143164 A1* | 10/2002 | Rotin | C07K 14/4702 536/23.1 |
| 2002/0160004 A1* | 10/2002 | Lyman | C12N 15/8509 707/E17.037 |
| 2002/0160974 A1* | 10/2002 | Banchereau | A61P 17/02 514/7.3 |
| 2003/0113341 A1* | 6/2003 | Lynch | A61K 39/0011 514/19.3 |
| 2006/0037089 A1* | 2/2006 | Tsai | A01K 67/0275 800/18 |
| 2010/0215644 A1* | 8/2010 | Fantl | G01N 33/5041 435/7.1 |
| 2011/0301056 A1* | 12/2011 | Nakamura | C07K 14/70503 435/6.12 |
| 2012/0177632 A1* | 7/2012 | Shinohara | A61K 31/7105 435/23 |
| 2012/0207795 A1* | 8/2012 | Zink | A61K 9/0019 977/773 |
| 2013/0156764 A1* | 6/2013 | Levis | A61K 31/7068 514/19.6 |
| 2013/0239239 A1* | 9/2013 | Jou | A61P 35/00 435/7.1 |
| 2015/0313878 A1* | 11/2015 | Robinson | A61K 31/713 435/375 |
| 2015/0329913 A1* | 11/2015 | Iavarone | G01N 33/57407 435/7.1 |
| 2017/0100462 A1* | 4/2017 | Wells | G01N 33/57426 |

(Continued)

FOREIGN PATENT DOCUMENTS

RU    2012126722 A    1/2014

OTHER PUBLICATIONS

Frank Oncogen 2017 36:1816 (Year: 2017).*

(Continued)

*Primary Examiner* — Changhwa J Cheu
(74) *Attorney, Agent, or Firm* — Henry D. Coleman; R. Neil Sudol

(57) ABSTRACT

The present invention is directed to the discovery that Rap1-GTP, Rac1-GTP and Flt3-L can be used as Biomarkers for the early detection of sepsis in patients suspected of a bacterial infection which presents as sepsis or is likely to produce sepsis. In particular, the present invention is directed to methods, assays and kits which may be used to distinguish sepsis (infection) from systematic inflammatory response caused by sterile inflammation in trauma patients. The method may be used to diagnose bacteria infection and/or sepsis and monitor therapy of a patient to allow modification of treatment and/or cessation of treatment.

35 Claims, 11 Drawing Sheets

(56) References Cited

U.S. PATENT DOCUMENTS

| | | | |
|---|---|---|---|
| 2017/0160281 A1* | 6/2017 | Aghvanyan | A61K 39/39533 |
| 2017/0304385 A1* | 10/2017 | Jin | A61K 38/162 |
| 2017/0319624 A1* | 11/2017 | Chute | A61K 35/51 |
| 2019/0161456 A1* | 5/2019 | Holinstat | C07D 233/84 |
| 2019/0309036 A1* | 10/2019 | Jun | A61K 35/17 |

OTHER PUBLICATIONS

Gao Nature Communication 2015 6:7721 (Year: 2015).*
Higgins Integr Biol 2015 7:229 (Year: 2015).*
Pearl AE, et al. Selective Inhibition of FLT3 by Gilteritinib in Relapsed/Refractory Acute Myeloid Leukemia: a Multicenter, First-in-human, Openlabel, Phase ½ Study. Lancet Oncol, 2017;18(8):1061-1075.
Schnoor M, et al. Actin dynamics in the regulation of endothelial barrier functions and neutrophil recruitment during endotoxemia and sepsis. Cell Mol Life Sci, 2017;74:1985-1997.
Buranda T, et al. Rapid parallel flow cytometry assays of active GTPases using effector beads. Analytical Biochemistry, 2013;442:149-157.
V. Bondu, et al. Elevated Cytokines, Thrombin and PAI-1 in Severe HCPS Patients Due to Sin Nombre Virus. Viruses 7 (2015) 559-89.
J.H. Foley, P.F. Cook, and M.E. Nesheim, Kinetics of Activated Thrombin-activatable Fibrinolysis Inhibitor (TAFla)-catalyzed Cleavage of C-terminal Lysine Residues of Fibrin Degradation Products and Removal of Plasminogen-binding Sites. Journal of Biological Chemistry 286 (2011) 19280-19286.
S. Talens, et al. Binding of carboxypeptidase N to fibrinogen and fibrin. Biochemical and biophysical research communications 427 (2012) 421-425.
J.B. Walker, et al. Proteolytic cleavage of carboxypeptidase N markedly increases its antifibrinolytic activity. J Thromb Haemost 6 (2008) 848-55.
O. De Henau, et al. Signaling Properties of Chemerin Receptors CMKLR1, GPR1 and CCRL2. PloS one 11 (2016) e0164179.
V. Wittamer, et al. Specific recruitment of antigen-presenting cells by chemerin, a novel processed ligand from human inflammatory fluids. The Journal of experimental medicine 198 (2003) 977-85.
W. Vermi, et al. Role of ChemR23 in directing the migration of myeloid and plasmacytoid dendritic cells to lymphoid organs and inflamed skin. The Journal of experimental medicine 201 (2005) 509-15.
J. Kaur, et al. Identification of chemerin receptor (ChemR23) in human endothelial cells: chemerin-induced endothelial angiogenesis. Biochemical and biophysical research communications 391 (2010) 1762-8.
G. Loirand, and P. Pacaud, Involvement of Rho GTPases and their regulators in the pathogenesis of hypertension. Small GTPases 5 (2014) 1-10.
N.J. Brown, et al. Comparative effect of angiotensin-converting enzyme inhibition and angiotensin II type 1 receptor antagonism on plasma fibrinolytic balance in humans. Hypertension 34 (1999) 285-90.
A. Dendorfer, W. Raasch, K. Tempel, and P. Dominiak, Comparison of the vascular and antiadrenergic activities of four angiotensin II type 1 antagonists in the pithed rat. Journal of hypertension 20 (2002) 1151-6.
R.M. Edwards, et al. Pharmacological characterization of the nonpeptide angiotensin II receptor antagonist, SK&F 108566. J Pharmacol Exp Ther 260 (1992) 175-81.
R.M. Edwards, et al. Characterization of renal angiotensin II receptors using subtype selective antagonists. J Pharmacol Exp Ther 260 (1992) 933-8.
D.J. Stearns-Kurosawa, et al. The Pathogenesis of Sepsis. Annu Rev Pathol, 2011;6:19-48.
Skibsted, S. et al. Biomarkers of endothelial cell activation in early sepsis. Shock 39, 427-432 (2013).
Kim, W.S. & Lee, H.J. Management of sepsis. J Korean Med Assoc 56, 819-826 (2013).
Hernandez, G., Bruhn, A. & Ince, C. Microcirculation in Sepsis: New Perspectives. Current vascular pharmacology 11, 161-169 (2013).
McAdow, M. et al. Preventing Staphylococcus aureus Sepsis through the Inhibition of Its Agglutination in Blood. PLoS pathogens 7 (2011).
Sun, H.M. The interaction between pathogens and the host coagulation system. Physiology 21, 281-288 (2006).
Van Der Poll, T. & Herwald, H. The coagulation system and its function in early immune defense. Thrombosis and haemostasis 112 (2014).
Wang, H.J. et al. Identification of four novel serum protein biomarkers in sepsis patients encoded by target genes of sepsis-related miRNAs. Clin Sci 126, 857-867 (2014).
Sankar, V. & Webster, N.R. Clinical application of sepsis biomarkers. J Anesth 27, 269-283 (2013).
Pierrakos, C. & Vincent, J.L. Sepsis biomarkers: a review. Critical care 14 (2010).
Faix, J.D. Established and novel biomarkers of sepsis. Biomark Med 5, 117-130 (2011).
Charles, P.E. & Gibot, S. Predicting outcome in patients with sepsis: new biomarkers for old expectations. Critical care 18 (2014).
Mihajlovic, D., et al. Use of presepsin and procalcitonin for prediction of SeptiFast results in critically ill patients. J Crit Care 40, 197-201 (2017).
Geissmann, F. et al. Development of monocytes, macrophages, and dendritic cells. Science (New York, N.Y 327, 656-661 (2010).
Randolph, G.J., Angeli, V. & Swartz, M.A. Dendritic-cell trafficking to lymph nodes through lymphatic vessels. Nat Rev Immunol 5, 617-628 (2005).
Shortman, K. & Naik, S.H. Steady-state and inflammatory dendritic-cell development. Nat Rev Immunol, 2007;7:19-30.
Steinman, R.M. & Banchereau, J. Taking dendritic cells into medicine. Nature 449, 419-426 (2007).
Schmidt, A., Caron, E. & Hall, A. Lipopolysaccharide-induced activation of beta2-integrin function in macrophages requires Irak kinase activity, p38 mitogen-activated protein kinase, and the Rap1 GTPase. Molecular and cellular biology 21, 438-448 (2001).
Ring, S. et al. Regulatory T cell-derived adenosine induces dendritic cell migration through the Epac—Rap1 pathway. J Immunol 194, 3735-3744 (2015).
Lagarrigue, F., Kim, C. & Ginsberg, M.H. The Rap1-RIAM-talin axis of integrin activation and blood cell function. Blood 128, 479-487 (2016).
Reinhart, K., et al. New Approaches to Sepsis: Molecular Diagnostics and Biomarkers. Clin Microbiol Rev 25, 609-634 (2012).
Lvovschi, V. et al. Cytokine profiles in sepsis have limited relevance for stratifying patients in the emergency department: a prospective observational study. PloS one 6, e28870 (2011).
Buranda, T. et al. Rapid parallel flow cytometry assays of active GTPases using effector beads.
Worbs, T., Hammerschmidt, S.I. & Forster, R. Dendritic cell migration in health and disease. Nat Rev Immunol 17, 30-48 (2017).
Van Der Poll, T., et al. The immunopathology of sepsis and potential therapeutic targets. Nat Rev Immunol (2017).
Levy MM, et al. Mortality Changes Associated with Mandated Public Reporting for Sepsis. The Results of the New York State Initiative. Am J Respir Crit Care Med. 2018; 198: 1406-12.
Meyer N, et al. Temporal Trends in Incidence, Sepsis-Related Mortality, and Hospital-Based Acute Care After Sepsis. Crit Care Med. 2018; 46: 354-60.
Prescott HC, et al. Temporal Changes in the Influence of Hospitals and Regional Healthcare Networks on Severe Sepsis Mortality. Crit Care Med. 2015; 43: 1368-74.
Cummings J, et al. Fit-for-purpose biomarker method validation for application in clinical trials of anticancer drugs. Br J Cancer. 2010; 103: 1313-7.
Cherfils J and Zeghouf M. Regulation of small GTPases by GEFs, GAPs, and GDIs. Physiol Rev. 2013; 93: 269-309.
Lemichez E and Aktories K. Hijacking of Rho GTPases during bacterial infection. Exp Cell Res. 2013; 319: 2329-36.

(56) References Cited

OTHER PUBLICATIONS

Simons PC, et al. Small Volume Flow Cytometry-Based Multiplex Analysis of the Activity of Small GTPases Methods Mol. Biol. 2018; 1821:177-195.
Fan Z, et al. Neutrophil recruitment limited by high-affinity bent beta2 integrin binding ligand in cis. Nat Commun. 2016; 7: 12658.
Diabate M, et al. *Escherichia coli* alpha-hemolysin counteracts the anti-virulence innate immune response triggered by the Rho GTPase activating toxin CNF1 during bacteremia. PLoS Pathog. 2015; 11: e1004732.
Clark LW, P.E. G, R M and K.L. M. User Protocol for Evaluation of Qualitative Test Performance; Approved Guideline EP12-A. CLSI. http://www.clsi.org/source/orders/free/ep12-a2.pdf . . . 2002.
Howard D. Using the Military Medical Acuity Model to guide patient care. Nursing. 2016; 46: 14-7.
D'Avignon LC, et al. Prevention of infections associated with combat-related burn injuries. J Trauma. 2011; 71: S282-9.

\* cited by examiner

Rap1-GTP, Rac1-GTP and FMS-LIKE TYROSINE KINASE 3 LIGAND (FLT3-L) AS BIOMARKERS FOR EARLY DETECTION OF SEPSIS

RELATED APPLICATIONS AND GRANT SUPPORT

This application is a United States national phase patent application based upon international patent application number PCT/US19/28165 of international filing date Apr. 18, 2019, which claims the benefit of priority of United States provisional application s.n. U.S. 62/660,635 filed 20 Apr. 2018 of similar title to the present invention, the entire contents of both applications are incorporated by reference herein.

This invention was made with government support under grant numbers R03AI092130, R2INS066429, 1P50GM085273 and R21 NS066435 awarded by the National Institutes of Health (NIH), MCB0956027, awarded by the National Science Foundation (NSF), OC110514, awarded by the Department of Defense (DOD) and NSF I-Corp 7775897 The government has certain rights in the invention.

FIELD OF THE INVENTION

The present invention is directed to the discovery that Rap1-GTP and FLT3-L and optionally Rac1-GTP can be used as biomarkers for the early detection of sepsis in patients exhibiting symptomology consistent with sepsis. In particular, the present invention is directed to methods, assays and kits which may be used to distinguish sepsis (infection) from systematic inflammatory response caused by sterile inflammation in trauma patients. The method may be used to diagnose bacteria infection and/or sepsis and monitor therapy of a patient to allow modification of treatment and/or cessation of treatment. Additional aspects of the invention relate to the use of these same biomarkers for the monitoring of therapy in the treatment of sepsis.

Background and Overview of the Invention

The clinical phenotype of sepsis is often indistinguishable from systematic inflammatory response caused by sterile inflammation in trauma patients. This ambiguity may result in overtreatment with lifesaving standard therapies of antibiotics when a bacterial pathogen can not be ruled out on a short timeline. This is because bacterial detection generally relies on a blood test and does not always detect or accurately measure localized infection burden. In complex injury cases involving trauma, the clinical picture is often confounded by the question of whether the patient is infected or is instead displaying signs of "sterile inflammation". Given that therapeutic intervention is quite different in each instance, it is important to have a sensitive measure for distinguishing when a patient is or becomes infected so that antibiotics and anti-inflammatory drugs can be appropriately administered. Sepsis affects patients from a broad demographic spectrum and across many disease states. Cases include the very young and elderly, the immunocompromised, those with cancer, those with trauma and other critically ill patients with co-morbid conditions. The estimated mortality rate of sepsis is 30% in the US.[1-4] Successful clinical intervention during sepsis depends on timely diagnosis that enables judicious administration of appropriate treatment regimens. Blood cultures remain the diagnostic gold standard for identifying bloodstream infections, yet suffer from the long lag time and low sensitivity in obtaining a positive result. The diverse range of microbial agents that cause sepsis, local sites of injury and infection and patient heterogeneity further confounds accurate tracking of the pathogenesis of this disease.[5-7] So far ~180 distinct potential biomarkers of sepsis are known.[8-12] The high number of targets has limited their prognostic value. Elevated procalcitonin and C-reactive protein have been used most widely, though have limitations in distinguishing sepsis from severe inflammatory disease, motivating continued search for biomarkers.[13] In an ongoing study, we have identified previously unreported early markers of bacterial infection associated with sepsis. In particular, we have identified Fms-like tyrosine kinase-3 ligand (Flt3-L) and activation of small GTPases such as Rap1, Rac1 and sometimes RhoA as early indicators of sepsis caused by bacterial infection. In addition, these markers are sensitive to the efficacy of antibiotic treatment and can thus be used as a clinical decision support tool for initiation or termination of antibiotic treatment.

It is well established that monocytes are central to the innate immune response to infections that cause sepsis. The host response to bacterial infections includes the release of inflammatory mediators that stimulate the differentiation of monocytes into dendritic cells and macrophages, which subsequently migrate from the blood into tissue infection sites.[14] At the infection sites dendritic cells are effective and versatile antigen-presenting cells for T cell activation and coupling to the adaptive immune response, while macrophages serve to clear damaged cells and bacteria.[15] At the more granular level, Flt3-L is a strong stimulator of monocyte differentiation into dendritic cells.[16,17] Flt3-L in turn stimulates activation of small GTPases such as Rap1, Rac1 and RhoA, the first two being particularly important in early sepsis diagnosis. GTPase activation is essential for the motility of leukocytes, involved in early response to host infection. Rap1 is needed for integrin-mediated cell adhesion and is a critical factor in the regulation of T-Cell and antigen-presenting cell interactions. (reference: Katagiri K, Hattori M, Minato N, Kinashi T Rap1 Functions as a Key Regulator of T-Cell and Antigen-Presenting Cell Interactions and Modulates T-Cell Responses. *Mol. Cell Biol.* 2002; 22:1001-1015). Rac1 and RhoA are central to cytoskeletal remodeling required for leukocyte motility and extravasation through tissue to points of inflammation (references: Cherfils J and Zeghouf M. Regulation of small GTPases by GEFs, GAPs, and GDIs. *Physiol Rev.* 2013; 93:269-309; Lemichez E and Aktories K. Hijacking of Rho GTPases during bacterial infection. *Exp Cell Res.* 2013; 319:2329-36.)

To establish a possible mechanistic link connecting GTPase activity, bacteria virulence factors and innate immune response to bacteria, we measured GTPase activity in cell lysates challenged cells with lipopolysaccharide (LPS) a Gram-negative bacterial endotoxin, which stimulates GTP binding to Rap1 in phagocytes and endothelial cells via CD14[18] (FIGS. 1A&B). In parallel, other cells were exposed to Flt-3L, which elicited GTP binding to Rap1 and Rac1 (FIGS. 1A&C). Given the in vitro associations between Flt-3L and Rac1-GTP, we hypothesized that bacterial infection stimulates coordinate-increases in Flt-3L and Rap1-GTP. Furthermore, based on our data we hypothesized that LPS found in Gram negative bacteria, is likely to synergistically upregulate Rap1-GTP in tandem with Flt-3L which stimulates the upregulation of both Rap1-GTP and Rac-GTP. These findings were subsequently built-upon and extended to a retrospective study of longitudinal samples from trauma patients who developed hospital acquired infections. The human plasma samples were analyzed for 41 common inflammatory mediators using the 41plex HCYT-MAG-60K-PX41 Cytokine kit, Human (Millipore, MA). In parallel, GTP loading of RhoA, Rac, and Rap1 was measured in cell lysates after their exposure to the plasma samples. The results showed coordinate induction of Flt-3L and Rap1-GTP and Rac1-GTP in 4 out of 5 tested samples (examples for tandem Flt3-3L and Rap1 and Rac1 are shown FIGS. 2, 3). As shown, the increase in the two biomarkers precedes the onset of clinically diagnosed bacterial infection (tdx in FIGS. 2B and 3B and 3D). We have previously disclosed a method of quantitative multiplex measurements of GTP binding to small GTPases. This enables the quantitation of GTP binding to multiplex beads used to analyze GTPase activity associated with cell activating agonists present in the plasma of our study cohort (FIG. 4 patients who develop infection post-admission, Patients 3, 10, and 13 or were septic on arrival (patient 14). Validation of the parallel induction of Flt-3L and Rap1 and or Rac1 ahead of clinical diagnosis of sepsis has important implications for the development of new biomarkers for early diagnosis of sepsis. The finding is the basis for a new testing system described in this invention that has utility for diagnosing and treating sepsis, monitoring therapy by determining the effectiveness of therapy and/or determining whether a change in the course of therapy is warranted and monitoring the efficacy of a therapeutic regimen and/or a novel compound or composition which has shown utility in vitro as a potential therapy for the treatment of sepsis.

BRIEF DESCRIPTION OF THE INVENTION

The present invention is directed to the discovery that the biomarkers Rap1-GTP and Flt-3L and optionally, Rac1-GTP may be used to provide an early diagnosis of sepsis (bacterial or other infection) prior to or in the absence of a positive blood culture. Furthermore the markers accurately and sensitively distinguish the onset of sepsis due to bacterial infection from a purely systemic inflammatory response (SIRS). Pursuant to the present invention, the biomarkers Rap1-GTP and Flt-3L and optionally Rac1-GTP are analyzed from biological samples (e.g., whole blood, serum, plasma, white blood cells or cell lysates derived from patient leukocytes) taken from a patient or subject suspected of having a bacterial infection, which presents as sepsis or is likely to present as sepsis and analyzed to determine the level of these biomarkers and compared to a standard (which can be the patient or subject at an early stage such as before the patient evidences an indication of a bacterial infection or a standard which is developed for a population of uninfected/normal patients) wherein levels of the biomarkers which are elevated compared to the standard are evidence that the patient has a bacterial infection which presents as sepsis or could worsen into sepsis and the patient is administered an antibiotic regimen consistent with a bacterial infection. In embodiments, an early indication of sepsis from an immunochromatography assay and/or an ELISA assay which provides an initial indication of upregulated or elevated concentrations of Rap1-GTP and Flt3-L and optionally, Rac1-GTP is further analyzed using flow cytometry, including multiplex GTPase assay (G-Trap) to quantify the biomarkers. In other embodiments, the analysis is partnered with devices to identify the particular bacterial infection in order that targeted antibiotic therapy may be used.

Pursuant to the present invention, it has unexpectedly been discovered that levels of expression of the biomarkers Rap1-GTP and Flt-3L, and optionally, Rac1-GTP are especially suited for bacterial/sepsis analysis in patients who are suspected of having a bacterial infection which is likely to produce sepsis or is in an early stage of sepsis before positive blood culture or is under treatment for sepsis. In all cases concrete evidence of ongoing infection, therapeutic responsiveness to treatment or lack thereof is critical for patient care. A positive test result would enable antibiotics to be administered to patients early in the infection stage or alert when an antibiotic regimen is not working and needs to be changed in order to avoid the damage, including death which occurs when bacterial infections and/or sepsis are left untreated.

While the expression of the biomarkers Rap1-GTP, Rac1-GTP and Flt-3L may be measured and analyzed by any assay method available in the art, preferred assays include point of care (POC) assays such as immunochromatograph assays as described herein, as well as multiplex assays (G-Trap) as described herein suited for clinical diagnostic labs, and as known in the art.

Thus, the present invention targets (Rap1-GTP and Flt-3L, and optionally, Rac1-GTP expression) are rationally selected on the basis of functional biology associated with early immunity as well as availability of unique measurement technology for the biomarkers. Coordinate measurement, validated utility in a retrospective study of septic patients, of Rap1-GTP and Flt-3L and optionally Rac1-GTP expression are critical for validity, which is confirmed by clinical results. The GTPase activity assays are based on a novel platform to foster commercialization of the GTPase activity assay platform (G-Trap). See, for example, Simons P C, Bondu V, Wandinger-Ness A and Buranda T. Small volume Flow Cytometry-Based Multiplex Analysis of the Activity of Small GTPases *Methods Mol. Biol.* 2018; 1821: 177-195; relevant portions of which are incorporated by reference herein.

Because bacterial infection elicits an innate immune response in the host, the immune response can be identified in patients who are suspected of having a bacteria infection and the patient can be placed on an antibiotic regimen earlier in the infection cycle to gain early control of the infection and minimize damage. Innate immunity includes the mobilization of dendritic cells, which are powerful antigen-presenting cells. Given the interdependence of monocyte differentiation and maturation into dendritic cells and dendritic cell migration to sites of infection, the inventors have hypothesized and shown that parallel measures of Flt-3L (inducer of dendritic cell mobilization) and Rap1-GTP (effector of integrin activation and motility) are effective temporal indicators of bacterial induced immune response. Thus, the measurement of Flt3-L and Rap1-GTP when compared with a standard and shown to be elevated at concentrations often at least 50% higher than a control and preferably at least twice the baseline level of each of the biomarkers in the patient or subject prior to indication of sepsis infection, provides an accurate early indication of sepsis which can be addressed by the administration of appropriate therapy (often a broad spectrum antibiotic regimen as described herein) to treat the patient for the sepsis infection (FIGS. 2-4).

Current approaches based on biomarkers of sepsis (inflammation: cytokines), host response (fever, tachycardia, tachypenoea; lab tests (WBC, CRP, etc.) present significant overlap with other pathologies and are not definitive for specifying a diagnosis of sepsis in a patient or subject. Procalcitonin (PCT): a promising biomarker upregulated within 2-3 hours of induction by endotoxin is not effective in an ICU setting where it is susceptible to false positives when trauma is present. The assay described here has been tested in an ICU setting using longitudinal samples drawn from trauma patients who develop sepsis during hospitalization, and demonstrated to sensitively and accurately presage positive blood cultures and lack of antibiotic responsiveness. The biomarkers that are measured herein are novel and not part of any analytical approach currently under consideration.

The invention will measure these markers using flow cytometry and/or using commercially available immunochromatographic kits that have been configured for Rap1-GTP and Flt3-L and optionally, Rac1-GTP as a rapid pre-screen assay for sepsis. In one embodiment, a determination of the levels of Rap1-GTP and Flt3-L and optionally, Rac1-GTP are made in a point-of-care facility utilizing ELISA assays and/or immunochromatographic assays as a first step followed by flow cytometry analysis (G-Trap analysis) to provide a more rigorous analysis of Rap1-GTP and Flt3-L and optionally, Rac1-GTP levels in biological samples (e.g., whole blood, serum, plasma, white blood cells or cell lysates derived from patient leukocytes) taken from a patient or subject who is believed to have sepsis or to be at risk for sepsis. Such patients are placed on antibiotic regimens to treat (inhibit the progression of and/or ameliorate) the infection, which gave rise to the sepsis diagnosis. In embodiments, the antibiotic regimen both reduces the progression of the infection and begins to ameliorate and reduce the infection. It is noted each step in the analysis can be performed once or twice a day (or more) per day for a number of days to assess if infection is still present and/or responsive to treatment in the patient.

The following points are noted in the present invention:
- If numbers for Rap1-GTP and Flt3-L and optionally measured Rac1-GTP are on the rise over a period of at least one day and up to several days compared to a standard (often the levels in a patient taken before the risk of infection or infection sets in) it is an indicator of active infection. This will require that an anti-sepsis antibiotic regimen be administered to the patient until such time as the infection resolves.
- If the numbers for Rap1-GTP and Flt3-L and the optionally measured Rac1-GTP, plateau in the presence of an antibiotic it means the antibiotic is not effective—the response is to change the antibiotic, this impacts antibiotic stewardship.
- If the numbers go down it means treatment is effective and one might consider how to best effect antibiotic stewardship noting that bringing the levels of Rap1-GTP and Flt3-L and the optionally measured Rac1-GTP down to a pre-infection baseline for at least a day and often several days will indicate resolution of the infection/sepsis and can inform when it is safe to discontinue antibiotic treatment. Interviews of physicians identify that this is a significant need and would significantly advance clinical care, which relies on empiric methods for antibiotic treatment protocols.

The present inventors have evidence that the tandem measurement of two markers, the Flt3-L cytokine ligand and Rap1-GTP and optionally, Rac1-GTP, can rapidly and specifically identify sepsis and be used to guide antibiotic stewardship (FIGS. 3 and 6). Rap1 GTPase activation and the Flt3 cytokine are highly sensitive to pathogen-associated agonists that dictate host immune responses. The inventors have developed a test to sensitively monitor these markers and have demonstrated utility of the test as a sensitive and specific measure of immune-mediated signaling in response to bacterial infection. A preferred embodiment of this test is described herein as a lateral flow assay which can measure at least Flt-3L and Rap1-GTP and preferably Flt-3L, Rap1-GTP and Rac1-GTP both qualitatively and quantitatively to establish that infection is producing/resulting in sepsis at an early stage or to monitor the impact of antibiotic therapy on the infection once sepsis is identified from the levels of Flt-3L and Rap1-GTP and optionally Rac1-GTP in the patient.

Pursuant to the present invention, these biomarkers decline in response to appropriate antibiotic treatment regimens, which can be quantitatively measured for purposes of monitoring/determining the effectiveness of therapy and allowing changes to a therapeutic regimen mid-treatment. Thus, the markers can be used to measure response to treatment and guide antibiotic time of treatment as well as inform on the suitability/efficacy of the antibiotic and the necessity of modification of the therapy. The clinical need for a sensitive and specific assay for monitoring sepsis and to guide antibiotic stewardship has been validated through market an NSF I-Corps funded market analyses and over 100 interviews with health care providers, pharmacists, device innovators, distributors product suppliers and clinical laboratory staff.

The Flt3-L, Rap1-GTP and optional Rac1-GTP markers (preferably all three biomarkers) can be assessed through a qualitative point of care test or a quantitative flow-based assay to provide specific and actionable results at the bedside. Thus, expression levels of these biomarkers in a patient undergoing a treatment regimen are measured and the measurements obtained are compared with a standard (which may be obtained from the patient prior to therapy or alternatively, from a known standard taken from a population of patients) whereupon measurements which are higher or not significantly lower than the standard may result in the initiation or modification of therapy and measurements which are significantly lower than a standard is an indication that the therapy employed is effective and/or successful.

In an embodiment, the invention is directed to a method for identifying sepsis or the likelihood of sepsis in a patient, the method comprising obtaining at least one biological sample (whole blood, serum, plasma, white blood cells or cell lysates derived from patient leukocytes, preferably serum for Flt3-L and lysates for Rap1-GTP and/or Rac1-GTP), measuring the levels of the biomarkers Flt3-L and Rap1-GTP and optionally Rac1-GTP in the samples and comparing the levels of the biomarkers with a standard, wherein a level of biomarkers in the patient sample which is higher than the standard is evidence that the patient's infection is likely to result in sepsis or the patient is in an early stage of sepsis such that sepsis therapy (as more fully described herein) is initiated. In a preferred embodiment, the method of identifying or diagnosing sepsis in a patient relies on a point of care (POC) assay, such as an ELISA sandwich assay or more often, a lateral flow assay as described in greater detail herein. The patient sample may be analyzed a single time or over a period of days (often twice a day) to monitor the patient's status and incipient disease state.

In an embodiment, the invention is directed to a method for monitoring therapy against sepsis in a patient, the method comprising obtaining at least two biological samples at different times (one sample taken earlier and one later, often at least half a day apart, often at least a day apart during the course of therapy, often once a day for several up to 5-7 days or more) during therapy of a patient diagnosed with sepsis or with an infection which is likely to develop into sepsis and is being treated with anti-sepsis therapy (especially including antibiotic therapy), measuring the levels of the biomarkers Flt3-L and Rap1-GTP and optional Rac1-GTP (preferably all three biomarkers) in the samples taken from the patient at the different times, comparing the levels of said biomarkers with a standard, determining that the levels of biomarkers in said samples and determining whether the anti-sepsis therapy of said patient should be continued, modified or terminated. In embodiments, one or more samples taken from a patient may be rigorously analyzed utilizing flow cytometry for providing a cytokine profile and/or a detailed analysis of Flt-3L concentration using a commercial cytokine kit or using G-Trap analysis for doing a detailed analysis of Rap1-GTP/Rac1-GTP including concentration (FIG. 4).

In an additional embodiment, the invention is directed to a point of care lateral flow assay for measuring Flt-3L and Rap1-GTP/Rac1-GTP levels in a biological sample (e.g., whole blood, serum, plasma, white blood cells or cell lysates of patient leukocytes) (FIG. 5). The assay comprises at least one sample and buffer zone where a sample is to be introduced onto the assay; a detector reagent or primary capture zone comprising Flt-3L or Rap-1-GTP and optionally Rac1-GTP detector reagents where Flt-3L and Rap1-GTP/Rac1-GTP analytes become bound to a monoclonal antibody specific for Flt-3L recognition or GST-effector proteins as bait for active GTPases; consisting of the minimal GTPase-binding domains (RBD) such as PAK-1 RBD (a Rac1 and Cdc42 effector) for Rac1-GTP, and RalGDS-RBD (a RAP1 effector protein) for RAP1-GTP. These biorecognition proteins (effectors or antibodies) are conjugated to color beads, quantum dots or colloidal gold. Flow-through analytes are thus specifically attached to the functionalized beads, in transit to the bead capture zone comprising a consecutive series of barrier lines of immobilized antibodies that recognize: 1) a different epitope of Flt3-L from the bead conjugate; 2) Rap1 or Rac1 specific antibodies, to arrest the movement of the analyte bearing beads/quantum dots at a capture line. Finally, fluid flow is contained by a zone which allows wicking of solution which has flowed through the assay. The capture profile of the reporter conjugates in the series of analyte lines will allow determination of the concentration of analyte in the sample when compared to a standard.

In preferred aspects, the lateral flow assay will also comprise non-specific IgG antibodies and/or non-specific GST fusion proteins to establish specificity of the assay. A preferred lateral flow assay useful in the present invention is set forth in FIGURES SA and B.

In preferred aspects, the detector reagents of the primary capture zone comprise an anti-Flt3-L IgG antibody bound to a color bead or quantum dot (the primary Flt3-L capture antibody is preferably EP1140Y from Novus Biologicals Centennial Colorado). Antibodies for the Flt-3L bead bioconjugate barrier lines to capture Flt-3L antibody reporter conjugates may preferably be Ab9688 rabbit polyclonal from Abcam or other Flt-3L IgG antibody. Bioconjugate proteins for the GTPase beads will consist of PAK-1 RBD for Rac1-GTP, and RalGDS-RBD for Rap1-GTP. Preferred antibodies for capturing GTPase bearing beads are Rap1A/Rap1B #4938 polyclonal rabbit from Cell Signaling Technology, 2399 Rap1/Rap1B (26B4) rabbit mAb from Cell Signaling Technology rabbit or Rap1A, clone 5F8, mouse mAB from Millipore-Sigma. In embodiments, the lateral flow assay of the present invention includes one or more non-specific IgG capture lines or non-specific GST fusion protein capture lines in order to define non-specific binding in the assay and increase efficiency.

In an embodiment, the level of Rap1-GTP in a patient's sample is determined using multiplex flow cytometry as described herein (FIG. 4). In an embodiment, the level of Flt3-L in a patient's sample is determined using flow cytometry.

In an embodiment, the present invention is also directed to a kit for carrying out the methods according to the present invention. This kit comprises the components and instructions necessary to quantify Flt-3L and Rap1-GTP and optionally Rac1 in order diagnose early stage sepsis and/or monitor the treatment of a patient with sepsis or at risk for sepsis. In an embodiment, the kit comprises a lateral flow assay as described herein in combination with other components.

In an embodiment, a lateral flow assay kit comprises:
1) A lateral flow cassette with single or multiple lanes for determining user specified analytes-FLT3-L, Rap1 GTP and optionally, Rac1 GTP;
2) Bioconjugate markers (color beads or quantum dots) functionalized with effector proteins or antibodies, for example, as described above or included in the flow cassette;
3) Lateral Flow cassettes available for qualitative analysis (color readout) or quantitative analysis (fluorescence readout);
4) Working Buffer reagents;
5) Instructions for using the assay; and
6) A graph setting forth standards for correlating an observed pattern of analyte captured at the analyte capture lines in the serial barrier zones, to analyte concentration in the test sample.

In other embodiments, the kit may comprise a syringe or other instrument for obtaining a sample from the patient and preparing the sample for introduction onto the lateral flow assay.

In embodiments, the present invention is directed to a Modular Multiplex G-Trap assay kit for measuring Rap1 and Rac1 and optionally, other GTPase targets in a sample comprising reagents for up to 96 assays/target (up to 384 assays for 4 targets in multiplex format) (Rap1, Rac1, and optionally RhoA, Arf6 etc.) comprising:
1) 1-4 sets of 96 assays with red color-coded beads, each functionalized with effector proteins for a desired GTPase target;
2) RIPA buffer, 20 ml bottle; PMSF, 1 mL vial; Protease inhibitors, 1 mL vial;
3) Rinse and flow buffer, 50 ml bottle;
4) Optional primary antibodies (these may be user provided);
5) Optional secondary antibody conjugated (may be user provided);
6) GST-GFP for troubleshooting, 1 mL vial; and
7) Manual, user guide with detailed protocols and troubleshooting suggestions.

Non-Limiting Embodiments of the Invention

In an embodiment, the present invention is directed to a method of treating a patient who has an infection which is causing sepsis or which has a likelihood of causing sepsis in the patient, the method comprising:
 obtaining a biological sample from a patient likely to have sepsis or an infection which will likely produce sepsis;
 measuring the expression levels of Rap1-GTP and Flt3-L in said sample;
 comparing the expression levels of Rap1-GTP and Flt3-L in said biological sample with a control or standard, wherein an expression level of Rap1-GTP and Flt3L which is greater than the control or standard is evidence that the patient has an infection in an early stage of sepsis or is likely to cause sepsis in said patient; and said patient is treated with anti-sepsis therapy if sepsis or a likelihood of sepsis is confirmed in said patient.

In an embodiment, the present invention is further directed to a method as described herein wherein the expression level of Rap1-GTP and Flt3-L which is at least 1.5 times the expression level of a control or standard evidences the presence of sepsis.

In an embodiment, the present invention is further directed to a method as described herein wherein the expression level of Rap1·GTP and FLT3L is twice to fifteen times or more the expression level of a control or standard, depending on the severity of sepsis in the patient.

In an embodiment, the present invention is further directed to a method as described herein wherein the expression level of Rap1-GTP and Fl3-L is twice to 8-10 times the expression level of a control or standard, depending on the severity of sepsis in the patient.

In another embodiment, the present invention is also directed to a method as described wherein Rac1-GTP biomarker in said sample is also measured and elevated compared to a standard, thus confirming the diagnosis of sepsis or likelihood of sepsis in said patient.

In still a further embodiment, the present invention is directed to a method as described herein wherein the expression level of said Rac1-GTP biomarker is at least 1.5 times the expression level of a control or standard further evidences the diagnosis of sepsis or likelihood of sepsis in said patient.

In an embodiment, the present invention is further directed to a method as described herein wherein the control or standard is established from the patient or subject during a period when the patient does not evidence sepsis.

In an embodiment, the present invention is further directed to a method as described herein wherein the control or standard is established from a non-infected patient or patient population.

In an embodiment, the present invention is further directed to a method as described herein wherein the infection is a bacterial infection and anti-sepsis therapy is antibiotic therapy.

In an embodiment, the present invention is further directed to a method as described herein wherein the expression is measured in an immunochromatography assay.

In an embodiment, the present invention is further directed to a method as described herein wherein the immunochromatography assay is a lateral flow assay.

In an additional embodiment, the present invention is further directed to a method as described herein wherein the Flt3-L expression is measured in a flow cytometer assay.

In still a further embodiment, the present invention is also directed to a method as described herein wherein the expression of Rap1-GTP is measured in a multiplex flow cytometer assay.

In yet another embodiment, the present invention is directed to a method as described herein wherein the expression of Flt3-L and Rap1-GTP is measured in a flow cytometer assay.

In still yet another embodiment, the present invention is further directed to a method as described herein wherein the expression of Flt3-L and Rap1-GTP is measured in a flow cytometer assay after being measured in said immunochromatography assay.

In an embodiment, the present invention is additionally directed to a method as described herein wherein the expression of Rap1-GTP is measured in a G-Trap multiplex flow cytometer assay.

In an embodiment, the present invention is further directed to a method as described herein wherein the measurement of biomarkers is coupled with further analysis to identify the specific causative agent responsible for the sepsis.

In an embodiment, the present invention is further directed to a method as described herein wherein the patient is administered an antibiotic in order to treat a bacterial infection as the causative agent of sepsis.

In an embodiment, the present invention is further directed to a method as described herein for determining whether or not a course of antisepsis treatment of a patient with an infection which has caused sepsis or is likely to cause sepsis in a patient is ineffective comprising measuring the expression of Rap1-GTP and Flt3-L in said patient at least once during said treatment, wherein an expression level of Rap1·GTP and Flt3-L which increases, remains the same or does not appreciably decrease during the course of treatment compared to a control or standard or compared to measurement(s) taken earlier in said treatment is evidence that the treatment is ineffective and said treatment should be changed; and said treatment is modified to effect therapy of said patient.

In an embodiment, the present invention is further directed to a method as described herein wherein said infection is a bacterial infection and said treatment comprises treatment with at least one antibiotic.

In an embodiment, the present invention is further directed to a method as described herein wherein the infection is a fungal infection and the treatment comprises treatment with at least one antifungal agent.

In an embodiment, the present invention is further directed to a method as described herein wherein the control or standard is established from the patient or subject during a period when the patient does not evidence sepsis or during a period earlier in the treatment for sepsis in said patient.

In yet another embodiment, the present invention is further directed to a method as described herein wherein Rac1-GTP biomarker in the sample is also measured and elevated compared to a standard, thus confirming the ineffectiveness of the treatment in the patient.

In an embodiment, the present invention is further directed to a method as described herein wherein the control or standard is established from an infected patient or patient population.

In yet another embodiment, the present invention is further directed to a method as described herein wherein the expression is measured in an immunochromatography assay.

In still another embodiment, the present invention is further directed to a method as described herein wherein the patient is administered a different regimen of antibiotics in order to treat a bacterial infection as the causative agent of sepsis.

In another embodiment, the present invention is further directed to a method as described for determining whether or not a course of treatment is effective in a patient with an infection which has caused sepsis or is likely to cause sepsis comprising measuring the expression of Rap1-GTP and Flt3-L in said patient at least once during said treatment, wherein an expression level of Rap1-GTP and Flt3-L which decreases during the course of antibiotics compared to a control or standard or an earlier measurement during the course of treatment in said patient is evidence that the treatment is effective and said treatment may be modified to a different less rigorous treatment, reduced and/or ceased.

In an embodiment, the present invention is further directed to a method as described herein wherein Rac1-GTP biomarker in the sample is also measured and reduced compared to a standard or earlier measurement of Rac1-GTP, thus confirming the diagnosis of the effectiveness of treatment of sepsis in the patient.

In an embodiment, the present invention is further directed to a method as described herein wherein the control or standard is established from the patient or subject during a period when the patient is established to have sepsis or during a period earlier in the treatment for sepsis in said patient.

In an embodiment, the present invention is further directed to a method as described herein wherein the control or standard is established from a non-infected patient or patient population.

In an embodiment, the present invention is further directed to a lateral flow assay comprising:
- at least one sample and buffer zone where a sample is to be introduced onto the assay;
- a detector reagent or primary capture zone where Flt3-L and Rap1-GTP analytes become bound to detector reagents comprising reporter antibodies or reporter proteins which are analyte specific and wherein each analyte specific antibody or protein is conjugated to a reporter to provide a Flt3-L antibody or protein reporter conjugate or a Rap1-GTP antibody or protein reporter conjugate after binding, each of which analyte bound antibody or protein report conjugate is capable of flowing through said assay;
- an analyte capture zone comprising analyte capture lines for Flt3-L and Rap1-GTP each of which capture lines comprises a support which is conjugated to a capture reagent comprising a capture antibody or protein which is specific for binding said Flt3-L antibody or protein reporter conjugate or said Rap1-GTP antibody or protein reporter conjugate and wherein said Flt3-L antibody or protein reporter conjugate or said Rap1-GTP antibody or protein reporter conjugate becomes concentrated after binding to said capture reagent at said capture lines; and
- a terminal wick zone which allows wicking of solution which has flowed through the assay to its terminal zone.

In an embodiment, the present invention is further directed to a method or assay as described wherein the biological sample is whole blood, serum, plasma, white blood cells taken from said patient or cell lysates derived from patient leukocytes.

In an embodiment, the present invention is further directed to an assay as described herein wherein the reporter is a color bead, a quantum dot or colloidal gold.

In an embodiment, the present invention is further directed to an assay wherein the reporter is a color bead or quantum dot.

In an embodiment, the present invention is further directed to an assay as described herein further comprising non-specific antibodies or non-specific proteins for enhancing the accuracy of the immunoassay.

In an embodiment, the present invention is further directed to an assay as described herein wherein the Flt3-L detector reagent comprises an anti-Flt3-L antibody.

In an embodiment, the present invention is further directed to an assay as described herein wherein the antibody is a monoclonal antibody.

In an embodiment, the present invention is further directed to an assay as described herein wherein the Rap1-GTP detector reagent is an effector protein comprising RaIGDS-RBD.

In an embodiment, the present invention is further directed to an assay as described herein wherein the effector protein is GST RaIGDS-RBD fusion protein.

In an embodiment, the present invention is further directed to an assay as described herein wherein the capture lines for Flt3L comprise supported antibodies capable of binding Flt3-L detector reagents.

In an embodiment, the present invention is further directed to an assay as described herein wherein the capture lines for Rap1-GTP comprise supported antibodies capable of binding Rap1-GTP detector reagents.

In an embodiment, the present invention is further directed to an assay as described herein further comprising non-specific IgG antibodies and/or non-specific GST fusion proteins to establish and/or increase specificity of the assay.

In an embodiment, the present invention is further directed to an assay as described herein further comprising in the detector reagent or capture zone a Rac1-GTP detector reagent comprising reporter antibodies or reporter proteins which are specific for Rac1-GTP and which are conjugated to a reporter to provide a Rac1-GTP antibody or protein reporter conjugate after binding which is capable of flowing through the assay, and in the capture zone an analyte capture line specific for Rac1-GTP comprising a support which is conjugated to a capture reagent comprising a capture antibody or protein which is specific for binding the Rac1-GTP detector reagent and wherein the Rac1-GTP detector reagent becomes concentrated in the capture line after binding to the Rac1-GTP capture reagent at the Rac1-GTP capture line.

In an embodiment, the present invention is further directed to an assay wherein the Rac1-GTP detector reagent comprises a reporter conjugated Rac1-GTP effector protein.

In an embodiment, the present invention is further directed to an assay as described herein wherein the effector protein is a GST PAK-1 RBD.

In an embodiment, the present invention is further directed to a multiplex lateral flow assay comprising:
- a lateral flow cassette with two or three lanes for determining the concentration of analytes in a biological sample obtained from a patient wherein the analytes comprise Flt-3L and Rap1-GTP, and optionally Rac1-GTP;
- a sample and buffer zone in each lane where a sample is to be introduced onto the assay;
- a detector or primary capture zone in each lane where FLT3L or Rap1-GTP analytes become bound to detector reagents wherein the detector reagents comprise antibodies or proteins which are analyte specific and wherein each detector reagent is conjugated to a reporter and each of the detector reagents is capable of flowing through the lane of the assay after binding said analyte;
- an analyte capture zone comprising analyte capture lines for FLT3L and Rap1-GTP each of which capture lines comprises a support which is conjugated to a capture reagent comprising a capture antibody or protein which is specific for binding the FTL3L detector reagent or the Rap1-GTP detector reagent and wherein the FLT3L detector reagent or said Rap1-GTP detector reagent becomes concentrated at the capture line after binding to said capture reagent; and
- a terminal wick zone which allows wicking of solution which has flowed through the assay to its terminal zone.

In an embodiment, the present invention is further directed to a multiplex assay as described herein further comprising in a separate lane of said assay or in the same lane that is used to measure the concentration of Rap1-GTP analyte in said biological sample; a detector reagent in said detector or primary capture zone specific for Rac1-GTP comprising antibodies or proteins which are Rac1-GTP specific and wherein said detector reagent is conjugated to a reporter and is capable of flowing through said lane of said assay after binding said analyte; and a capture reagent comprising a capture antibody or protein which is specific for binding said Rac1-GTP bound detector reagent wherein said capture reagent is bound to a support at a capture line in said analyte capture zone of said lane and said Rac1-GTP bound detector becomes concentrated after binding to said capture reagent at said capture line.

In an embodiment, the present invention is further directed to an assay as described herein wherein the detector reagent and capture reagent for Rac1-GTP is in the same lane as the detector reagent and capture reagent for Rap1-GTP.

In an embodiment, the present invention is further directed to an assay as described herein wherein the detector reagent and capture reagent for Rac1-GTP is in a separate lane from the detector reagent and capture reagent for Rap1-GTP.

In still a further embodiment, the present invention is also directed to a kit for diagnosing early sepsis in a patient with an infection in early sepsis or an infection likely to produce sepsis comprising a Modular Multiplex G-Trap assay kit for measuring Rap1, Rac1 and optionally, other GTPase targets in a sample comprising reagents for up to 96 assays/target and up to 384 assays for 4 targets in multiplex format comprising:
1) 1-4 sets of 96 assays with red color-coded beads, each functionalized with effector proteins for a desired GTPase target;
2) RIPA buffer, buffer bottle; PMSF; and protease inhibitors;
3) Rinse and flow buffer, buffer bottle;
4) Optional primary antibodies (these may be user provided);
5) Optional secondary antibody conjugated (may be user provided);
6) GST-GFP for troubleshooting, 1 mL vial; and
7) Manual, user guide with detailed protocols and troubleshooting suggestions.

In still a further embodiment, the present invention is directed to a lateral flow assay kit comprising:
1) A lateral flow cassette with single or multiple lanes for determining user specified analytes Flt3-L, Rap1-GTP and optionally, Rac1-GTP;
2) Bioconjugate markers comprising reporters (e.g., color beads, quantum dots, colloidal gel) functionalized with effector proteins or antibodies, for each of the analytes to be measured;
3) Lateral Flow cassettes available for qualitative analysis (color readout) or quantitative analysis (fluorescence readout);
4) Working Buffer reagents;
5) Instructions for using the assay; and
6) A graph setting forth standards for correlating an observed pattern of analyte captured at analyte capture lines in the serial barrier zones of said lateral flow cassettes, to analyte concentration in the test sample.

BRIEF DESCRIPTION OF THE FIGURES

FIG. 3C shows elevation of Rac1 activity following a pattern consistent with hypotension as described in FIG. 6.

DETAILED DESCRIPTION OF THE INVENTION

Figure 1:
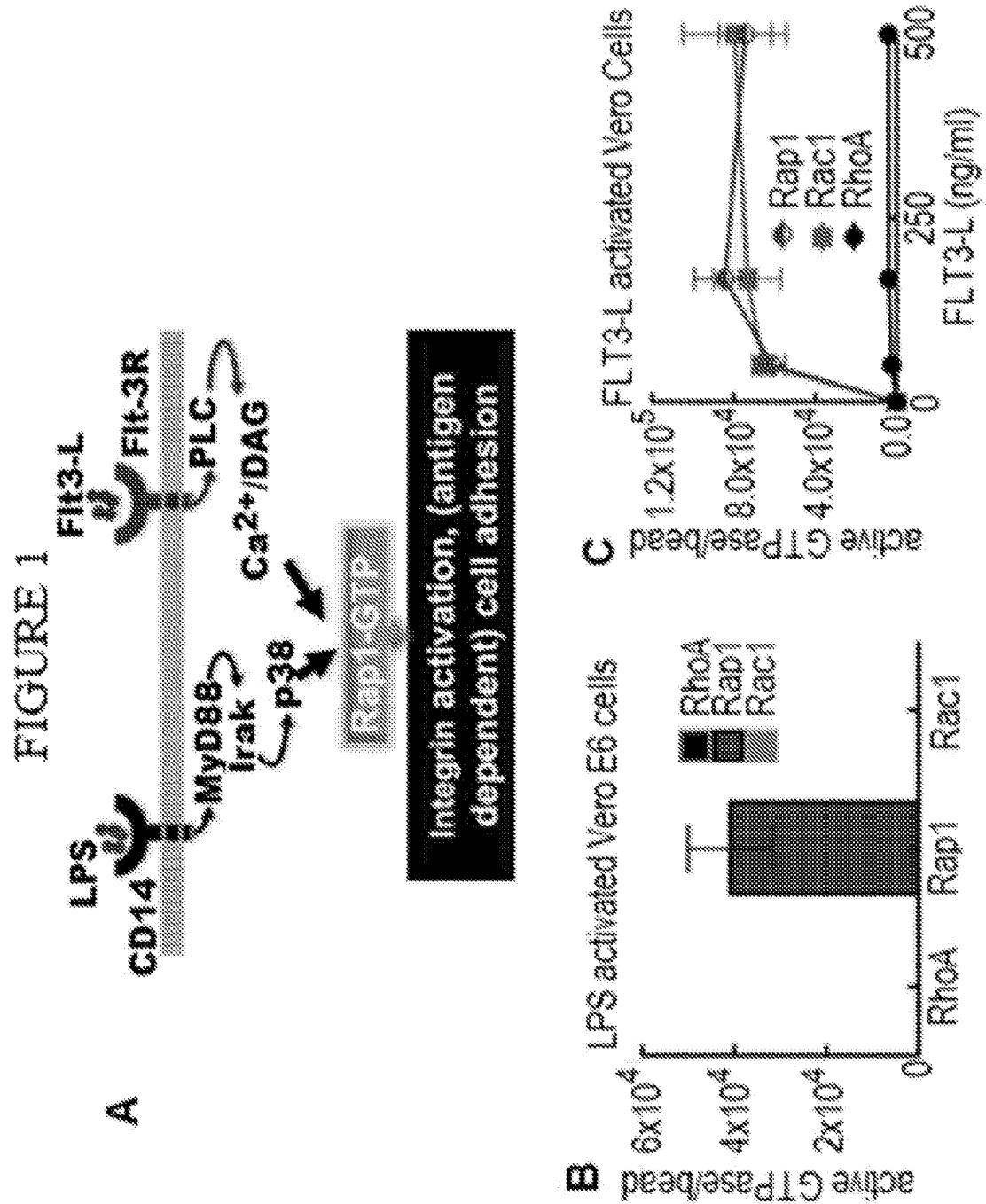
FIG. 1A shows a model of bacterial lipopolysaccharide (LPS) and Flt3-L cytokine-induced signaling pathways leading to activation of Rap1 mediated integrin activation and cell adhesion. B. LPS induced GTP loading of Rap1 in Vero E cells. C. Flt-3L induced GTP binding to Rap1 in endothelial cells. GTPase activity was measured in cell lysates after the cells were exposed to LPS or Flt-3L for 30 min.

The following terms shall be used throughout the specification to describe the present invention. Where a term is not specifically defined herein, that term shall be understood to be used in a manner consistent with its use by those of ordinary skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention. In instances where a substituent is a possibility in one or more Markush groups, it is understood that only those substituents which form stable bonds are to be used.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a." "and" and "the" include plural references unless the context clearly dictates otherwise.

Furthermore, the following terms shall have the definitions set out below.

"Sepsis-associated biomarker" as used to describe the present invention includes Rap1-GTP and Flt3-L and optionally Rac1 and relevant isoforms thereof. "Rap1-GTP" refers to canonical human Rap1-GTP and its isoforms thereof and "Flt3-L" refers to canonical human Flt3-L and its isoforms thereof. In preferred aspects of the invention, the canonical form of human FLTL3 and Rap1-GTP is measured. In other embodiments, Rac1 is optionally measured to confirm the increase in FLT3-L concentration.

The terms "RAP1, RAP1A or RAP1A Gene" refer to the gene encoding a small cytosolic GTPase protein ("Rap1 GTPase" or "Rap1") that acts like a cellular switch and is vital for effective signal transduction. RAP1 (the gene) is a member of RAS Oncogene Family, GTP-Binding Protein Smg P21A, Ras-Related Protein Rap-1A,Ras-Related Protein Krev-1, C21KG, G-22K, KREV1, KREV-1, SMGP21, RAP1. Pursuant to the present invention Rap1 (Rap1GTPase) protein binds to GTP pursuant to its upregulation by Flt3-L and forms Rap1-GTP, which is a biomarker (in addition to Flt3-L and optionally Rac1-GTP) measured pursuant to the present invention. It has been discovered that Rap1-GTP is a key indicator of the progression of a sepsis caused by bacterial infection in a patient or subject. The amino acid sequence for human Rap1 referred to in the present invention is found in GenBank under the accession number ABA64473. Rap1 binds to GTP in response to bacterial products or the activation of cytokine Flt3 upon infection, and is used as a measure of the presence of infection for the diagnosis of sepsis in humans in the present invention. In particular, it is the production of lipopolysaccharide from an infectious agent (Gram negative bacteria, virus, fungus, among others) in the blood of a patient or subject which upregulates/increases the presence or concentration of Rap1-GTP which is the activated biomarker Rap1-GTP of the present invention. Rap1-GTP is responsible for inducing Flt3-L (cytokine) which is also measured pursuant to the present invention. In the case of veterinary applications, the Rap1-GTP which is measured is that Rap1-GTP which is specific to the species or cross-reactive with the species of animal being diagnosed (dog, cat, domesticated animal such as a horse, cow, pig, etc.) for sepsis. In embodiments, the species is a dog or horse. In certain embodiments, Rac1 (Ras-related C3 botulinum toxin substrate 1), which is upregulated by the increase in Flt3-L may also be measured as a secondary confirmation of the results obtained for the measurement of Flt3-L. The measurement of Rac1 pursuant to the present invention is also species specific.

Thus, it has been discovered pursuant to the present invention that the production of lipopolysaccharide (endotoxin) by an infectious agent (bacterial, virus, fungus, etc.) in the blood of an infected patient or subject leads to the activation of Rap1 cystosolic protein, through the binding of GTP and a resultant conformation change that is detected in the assay by a specific effector protein binding interaction with RalGDS. Rap1-GTP is responsible for the induction of Flt3-L, the second of the two sepsis biomarkers which are measured pursuant to the present invention. Flt3-L induces Rac1 in a delayed manner, which also may be measured pursuant to the present invention to further confirm the diagnosis and/or monitoring of treatment.

Figure 9:
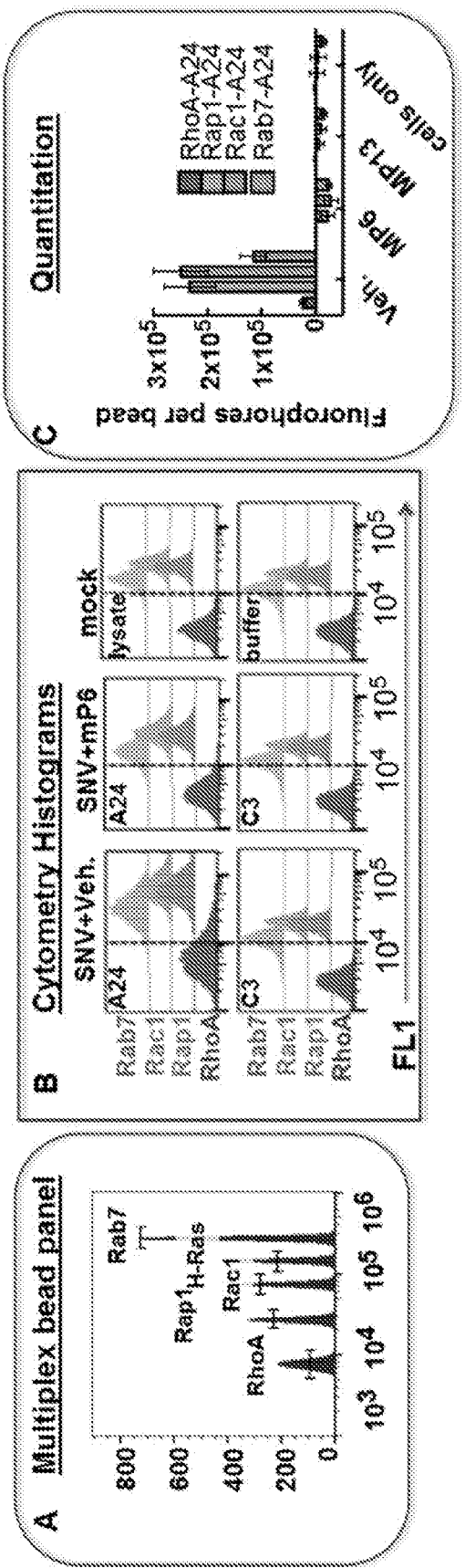
FIG. 9 shows: A. a multiplex bead panel; B a cytometry histogram panel and C a quantification panel for G-Trap multiplex assay. The G-Ttrap assay which is used here is described and exemplified in Simons P C, Bondu V, Wandinger-Ness A and Buranda T. Small volume Flow Cytometry-Based Multiplex Analysis of the Activity of Small Methods Mol. Biol. 2018; 1821:177-195.

The term "FMS-like tyrosine kinase 3 ligand", "FLT3-L", "Flt3-L" or "Flt3-L" refers to a hematopoietic four helical bundle cytokine is structurally homologous to stem cell factor (SCF) and colony stimulating factor 1 (CSF-1) and demonstrated four conserved cysteines and two glycosylation sites. Flt3-L naturally is a non-disulfide-linked homodimer with multiple isoforms. The extracellular portion is approximately 160 amino acid residues in length and the cytoplasmic segment is approximately 20-30 amino acid residues in length. The canonical sequence of human Flt3-L is UniProtKB-P49771-1. This is the Flt3-L biomarker which is identified in assays pursuant to the present invention in order to identify the risk of sepsis in a human patient or subject. In the case of veterinary applications, the Flt3-L which is measured is that Flt3-L which is specific to the species of animal being diagnosed (dog, cat, domesticated animal such as a horse, cow, pig, etc.) for sepsis. In embodiments, the species is a dog or horse, cat, pig or cow. In embodiments, Flt3-L is measured in the present invention in a lateral flow assay as described herein or using flow cytometry analysis as described in greater detail herein and as presented in FIG. 9 hereof.

Glutathione (GSH), a ubiquitous tripeptide, is an important cellular constituent, and measurement of reduced and oxidized glutathione is a measure of the redox state of cells. Glutathione-S-transferase (GST) fusion proteins, used in embodiments pursuant to the present invention, bind naturally to beads derivatized with glutathione, and elution of such bead-bound fusion proteins with buffer containing millimolar glutathione is a commonly used method of protein purification. GST fusion proteins may be used in embodiments in the present invention, in particular to capture analytes in lateral flow assays as described herein or in flow cytometry assays which may be used to measure Flt3-L levels in a biological sample (serum, plasma, white blood cell fraction or lysate thereof) taken from a patient, including multiplex assays, which are preferably used to measure Rap1-GTP and/or Rac1 (which is often optionally measured to confirm Flt3-L measurements). Many protein-protein interactions have been established by using GST fusion proteins and measuring binding of fusion protein binding partners by GST pulldown assays. Tessema, et al., "Glutathione-S-transferase-green fluorescent protein fusion protein reveals slow dissociation from high site density beads and measures free GSH", *Cytometry*, 69A: 326-334. doi: 10.1002/cyto.a.20259.

Reagents which specifically bind to the sepsis associated-biomarkers" Rap1-GTP and Flt3-L include biomarker protein purification reagents, antibodies to the biomarker polypeptides or peptides thereof, nucleic acid primers specific for genes which express the biomarkers, arrays of biomarker-related nucleic acid probes, signal producing system reagents, etc. Useful reagents include arrays that comprise probes, e.g. arrays of antibodies or arrays of oligonucleotides; or other reagents that may be used to detect the expression of these biomarkers. Those of ordinary skill in the art are familiar with how to identify and make the aforementioned reagents. See e.g. Spiegel, et al., Direct Targeting of Rab-GTPase-Effector Interactions, *Angewandte Chemie* International Edition Volume 53, Issue 9, pages 2498-2503 Feb. 24, 2014; Kahn, et al., "Structural Biology of Arf and Rab GTPases' Effector Recruitment and Specificity", *Structure* 21, Aug. 6, 2013 and other references, including Buranda, T. et al., *Analytical biochemistry* 144, 149-157 (2013).

The basics of flow cytometry and multiplexed flow cytometry are well-known to those of ordinary skill in the art. See e.g. the technical description and supporting references cited at the website: einstein.yu.edu/research/facilities/facs/page.aspx?id=22632. A useful summary of certain types of multiplexed flow cytometry assays is provided in U.S. Patent, Sklar, Simons Wandinger-Ness U.S. Pat. No. 7,785,900 B1 for use of GST-proteins immobilized on beads Issued 2010 and Application Document No. 20140206008 as follows. "Laminex MultiAnalyte Profiling (xMAP) technology, previously known as FlowMetrix and LabMAP (Elshal and McCoy, 2006), is a multiplex bead-based flow cytometric assay that is gaining recognition as a method for analyte quantitation. This technology utilizes 5.6-micron polystyrene beads that are internally dyed with different intensities of red and infrared fluorophores. Currently there are 100 beads, each with a unique spectral make up which allows the mixing of several bead sets and, in theory, enabling the detection of up to 100 different analytes per assay (Vignali, D. A. A., *J Immunol Methods,* 243:243-255 (2000)). The beads can be bound by various capture reagents such as antibodies, oligonucleotides, and peptides, therefore facilitating the quantification of various proteins, ligands, DNA and RNA (Fulton, R. J. et al., Clin Chem, 43:1749-1756 (1997); Kingsmore, S. F., Nat Rev Drug Discov, 5:310-321 (2006); Nolan, J. P. and Mandy, F., Cytometry Part A, 69A: 318-325 (2006)). The assays are run on a 96-well plate format, followed by detection on a Luminex 100 instrument. As the beads run through the instrument, the internal dyes are excited by a laser which results in the classification of each bead. Another laser excites the reporter dye which is directly proportional to the amount of analyte bound to each bead (Vignali, D. A. A., J Immunol Methods, 243:243-255 (2000); Ray, C. A. et al., J Pharma Biomed Anal, 36:1037-1044 (2005)). The resulting fluorescence is recorded by the instrument which then provides the median fluorescence unit obtained from measuring 100 beads. Luminex xMAP technology has many applications including protein expression profiling, gene expression profiling, genotyping, immunodiagnostics, and genetic disease diagnostics. Although single-plex bead-based assays have been available for a long time; technological developments have enhanced the development of multiplex bead-based assays enabling the utilization of this method for quantitation of a panel of protein markers simultaneously (Linkov, F. et al., Cancer Epidemiol Biomarkers Prev, 16:102-107 (2007); Prabhakar, U. et al., J Immunol Methods, 260:207-218 (2002)). The advantage of Luminex xMAP technology lies in its high sensitivity, throughput and efficiency (Vignali, D. A. A., J Immunol Methods, 243:243-255 (2000); DuPont, N. C. et al., J Reprod Immunol, 66:175-191 (2005)). Significant reduction in time and costs results from multiplexing when compared to ELISA. ELISA is more expensive and time-consuming to perform when many proteins are to be measured using many single-plex protein specific assays (de Jager, W. and Rijkers, G. T., Methods, 38:294-303 (2006)). On the contrary, many protein analytes can be measured by the multiplexed bead-based assay with a single plate. This is extremely important for clinical studies where sample volumes are limited (Liu, M. Y. et al., Clin Chem, 51:1102-1109 (2005)). Bead-based assay is more accurate because the median fluorescence is obtained from the readout of at least 50 to 100 beads. Thus each bead is functioning as a duplicate, making this assay more reliable (Vignali, D. A. A., J Immunol Methods, 243:243-255 (2000); Kettman, J. R. et al., Cytometry, 33:234-243 (1998))."

Multiplexed flow cytometric assays of the invention can use, e.g. 2, 4, 8, 16, 32, 64, 128, 256, or 12, 24, 36, 48 or 60 distinct sets of fluorescent spheres (beads) or microspheres and a standard benchtop flow cytometer interfaced with a personal computer containing a digital signal processing board and programmed with a variety of operating software. Individual sets of beads or microspheres (microbeads) can be modified with reactive components such as antigens, antibodies, or oligonucleotides, and then mixed to form a multiplexed assay set. The digital signal-processing hardware and software control the flow cytometer and perform real-time data processing, allowing multiple independent reactions to be analyzed simultaneously in qualitative and quantitative immunoassays for multiple serum proteins in both capture and competitive inhibition assay formats.

Multiplexed beads can be assigned to two or more groups which perform distinct assays and are distinguished by characteristics that enable distinct detection of assay group results. Bead size can be a distinguisher; beads are defined by distinct sub-sizes and are grouped into distinct sub-ranges, e.g. 2, 4, 8, 16, 32, 64, 128 sub-ranges, each of which conducts a unique assay. Particle size sub-ranges and mean diameter spacing of adjacent sub-ranges permit differentiation of the sub-ranges. Preferred sub-ranges can vary by about +/−5% CV or less of the mean diameter, where CV is the coefficient of variation and is defined as the standard deviation of the particle diameter divided by the mean particle diameter times 100 percent. Minimum spacing between mean diameters among the various sub-ranges can depend on bead size distribution and flow cytometry sensitivity. Fluorescence differentiation is achieved by using various fluorescent materials in the beads having different fluorescent emission spectra. Fluorescence can distinguish sub-groups and serve as an assay detector.

"A gate in cytometry" is a set of value limits (boundaries) that serve to isolate a specific group of cytometric events from a large set. Gates can be defined by discrimination analysis, or can simply be drawn around a given set of data points on a print-out and then converted to a computer-useful form. Gates can be implemented with a physical blinder. Gates may be used either to selectively gather data or to segregate data for analysis. Gates are divided mathematically into inclusive gates and exclusive gates. Inclusive gates select data that falls within the limits set, while exclusive gates select data that falls outside the limits. A live gate is a term used for a process that prevents the acquisition by the computer of non-selected data from the flow cytometer. (see, for example, Osborne, G. W. (2000) "Regions and Gates" Flow Cytometry Software Workshop: 2000, page 3)." See U.S. Patent Application Document No. 20120083007.

Other types of assays besides flow cytometric assays (e.g. ELISA, RIA, Western blot, luminescent immunoassay and fluorescent immunoassay as well as immunochromatography) can be used to measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies; A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Certain diagnostic and screening methods of the present invention utilize an antibody, preferably, a monoclonal antibody, capable of specifically binding to a protein as described herein or active fragments thereof. The method of utilizing an antibody to measure the levels of protein allows for non-invasive diagnosis of the pathological states of sepsis or viral hemorrhagic fever infections. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of protein in sample. In a particular embodiment, the antibodies of the present invention are used to detect and to measure the levels of protein present in a plasma sample or a sample in which white blood cells from a patient or subject have been lysed.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

Antibodies or antibody fragments employed in such screening tests may be free in solution, affixed to a solid support, borne on a cell surface, or located intracellularly. The blocking or reduction of biological activity or the formation of binding complexes between the disease-related protein and the agent being tested can be measured by methods available in the art.

Other techniques for identifying and quantifying biomarkers pursuant to the present invention provide for a high throughput screening of samples which measure the expression and/or activity of a disease, are known in the art. For example, microarrays carrying test samples can be prepared, used, and analyzed using methods available in the art. See, e.g., Shalon, D. et al., 1995, International Publication No. WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Other screening techniques, which can also serve to determine the presence and levels of sepsis associated biomarkers are well-known to those or ordinary skill in the art. See, e.g., Enna et al., eds., 1998, Current Protocols in Pharmacology, John Wiley & Sons, Inc., New York N.Y. Assays will typically provide for detectable signals associated with the binding of the biomarkers to a protein or cellular target. Binding can be detected by, for example, fluorophores, enzyme conjugates, and other detectable labels well known in the art. The results may be qualitative or quantitative.

To determine specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody. Various labels can be used such as radioisotopes, enzymes, fluorescers, chemiluminescers, particles, etc. There are numerous commercially available kits providing labeled anti-hIg, which may be employed in accordance with the manufacturer's protocol.

In one embodiment, a kit can comprise: (a) at least one reagent which is selected from the group consisting of (i) reagents that detect a transcription product of the gene coding for a protein marker as described herein (ii) reagents that detect a translation product of the gene coding for proteins/biomarkers, and/or reagents that detect a fragment or derivative or variant of said transcription or translation product; (b) instructions for diagnosing, or prognosticating a disease, or determining the propensity or predisposition of a subject to develop such a disease or of monitoring the effect of a treatment by determining a level, or an activity, or both said level and said activity, and/or expression of the transcription product and/or the translation product and/or of fragments, derivatives or variants of the foregoing, in a sample obtained from said subject; and comparing the level and/or the activity and/or expression of said transcription product and/or said translation product and/or fragments, derivatives or variants thereof to a reference value representing a known disease status (patient) and/or to a reference value representing a known health status (control) and/or to a reference value; and analyzing whether said level and/or said activity and/or expression is varied compared to a reference value representing a known health status, and/or is similar or equal to a reference value representing a known disease status or a reference value; and diagnosing or prognosticating a disease, or determining the propensity or predisposition of said subject to develop such a disease, wherein a varied or altered level, expression or activity, or both said level and said activity, of said transcription product and/or said translation product and/or said fragments, derivatives or variants thereof compared to a reference value representing a known health status (control) and/or wherein a level, or activity, or both said level and said activity, of said transcription product and/or said translation product and/or said fragments, derivatives or variants thereof is similar or equal to a reference value and/or to a reference value representing a known disease stage, indicates a diagnosis or prognosis of a disease, or an increased propensity or predisposition of developing such a disease, a high risk of developing signs and symptoms of a disease.

Reagents that selectively detect a transcription product and/or a translation product of the gene coding for proteins can be sequences of various length, fragments of sequences, antibodies, aptamers, siRNA, microRNA, and ribozymes. Such reagents may be used also to detect fragments, derivatives or variants thereof.

The term "patient" or "subject" is used throughout the specification within context to describe an animal, generally a mammal, especially including a domesticated animal and preferably a human, to whom a treatment, including prophylactic treatment (prophylaxis) is provided. For treatment of those infections, conditions or disease states which are specific for a specific animal such as a human patient, the term patient refers to that specific animal. In most instances, the patient or subject is a human patient of either or both genders.

The term "effective" is used herein, unless otherwise indicated, to describe an amount of a compound or component which, when used within the context of its use, produces or effects an intended result, whether that result relates to the prophylaxis and/or therapy of an infection and/or disease state or as otherwise described herein. The term effective subsumes all other effective amount or effective concentration terms (including the term "therapeutically effective") which are otherwise described or used in the present application.

The term "lateral flow assay" is used to describe a chromatographic system which provides a separation of components of a mixture on the basis of differences in their movement through reaction membrane and an immunochemical reaction (between an antibody-antigen or a nucleic acid target analyte). It is based on the movement of sample across the membrane via capillary force. The standard lateral flow assay has four parts: a sample pad, the area on which sample is dropped; conjugate pad, on which labeled tags combined with biorecognition elements; reaction membrane (usually nitrocellulose membrane), on which location containing test line and control line for target Antibody-antigen interaction of DNA-probe DNA hybridization; and an absorbent pad, which reserves waste. (See, for example, Bahadir, et al., *Trends in Analytical Chemistry*, 82, 2016, pp. 286-306, and Posthuma-Trumpie, et al. *Anal. Bioanal. Chem.* (2009) 393:569-582). The principal of lateral flow assay is similar to ELISA sandwich method, the only difference is in that immunological reaction is carried out on the chromatographic paper by capillary action. For this system, two kinds of capture against proteins are used. One of the proteins (e.g. antibodies) is immobilized on the chromatographic paper, and the other is labeled with colloidal gold, quantum dots or color beads and infiltrated into sample pad in the detector reagent zone. An immunochromatographic unit is completed by attaching the sample pad at the end of the membrane. A preferred assay for use in the present invention is a custom design immunoassay based on off-the-shelf components obtained from DCNdx.com. The method as described in prior patents (e.g. WO 98/39657), several primary and review literature sources, comprises a lateral flow matrix presenting, 1) a sample loading zone, 2) a reagent zone, and 3) one or more serially oriented capture zones.

Figure 2:
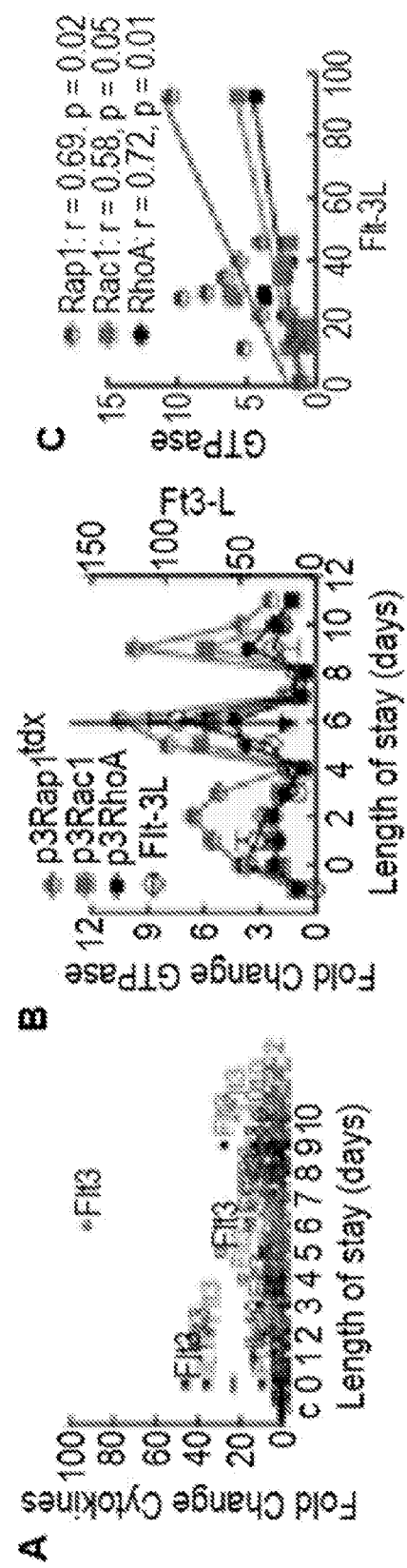
FIG. 2 shows that bacterial infection is positively correlated to elevated Flt3-L and small GTPase activity. Patient #3, an elderly woman (88 years old) was run over by a car. The patient required mechanical ventilation due to hypoxemia and hypercapnia related to traumatic lung injury (pulmonary contusion) and massive chest wall injury. Her initial hospital course was indicative of SIRS and endothelial barrier dysfunction with the requirement for 8 liters crystalloid infusion in the first 48 hours, in conjunction with vasopressor support (norepinephrine) to improve her mean arterial pressure, she exhibited no active bleeding as her clinical coagulation parameters (PT/PTT, INR, and platelet count) remained within normal limits during admission. Later in her hospital course, she developed signs of sepsis including leukocytosis (>12k WBC on day 6), fever, refractive hypotension that was not responsive to fluid administration, requirement for vasopressor support (norepinephrine and vasopressin), radiographic evidence of pneumonia, and >100 fold increase in c-reactive protein, a biomarker of non-resolving inflammation. Cultures of blood, sputum, and urine were obtained, and sputum culture was positive for bacterial pathogen. Blood transfusion was administered on day 7 of admission due to the development of acute anemia. She developed progressive multiple organ dysfunction including pulmonary dysfunction, and hepatic failure. The patient expired on post-injury day 10. A. A plot of cytokines measured with 41plex HCYTMAG-60K-PX41 cytokine kit indicating predominant expression of Flt3-L relative to other cytokines in serial plasma samples of trauma Patient 3. Examination of the longitudinal changes in the expression of 41 cytokines present in blood samples collected during Patient #3's ten day length of stay (LOS) in the ICU indicated significant increases in Flt-3L expression and peaks on three occasions during the patient's LOS. Firstly, on day 2 which coincided with the clinical need for crystalloid infusion. Secondly, Flt3-L peaked on day 6, when the patient's blood culture was determined to be positive for bacterial pathogen. Thirdly, Flt3-L peaked two days after a blood transfusion following refractory hypotension. B. In parallel, we used the same serial plasma samples from Patient #3 to stimulate the activity of small GTPases in telomerase-immortalized human microvascular endothelium cell line (TIME). GTP-binding Rap1, Rac1 and RhoA, recapitulated the same pattern of Flt3-L upregulation over the same period, and showed a positive correlation between Flt3-L upregulation and Rap-1 activation (FIG. 2C). C. Spearman rank correlation plot shows positive correlation between Flt3-L expression and GTPase activity. D. Cytokine profile of Patient #19.52 year old man admitted after shotgun wound to the abdomen. Injuries include low grade liver lacerations, high grade right renal injury with hilar disruption requiring nephrectomy, zone 1 retroperitoneal hematoma without evidence of vascular injury, hepatic flexure colonic mesenteric hematoma, and traumatic abdominal wall hernia of approximately 3 cm, right $5^{th}$ through $8^{th}$ rib fractures, L2-3 vertebral body fractures. Underwent multiple laparotomies with eventual closure. Underwent full 14 day collection including time zero specimen. ICU LOS was 7 days. No frank sepsis during enrolled timeframe but did develop UTI several days after last collection. The graph presented in D shows that patient 19, with a shot gun blast to the abdomen, was aseptic during length of stay (LOS) at UNMH. E. Plot of Rap1 and Flt3-L measured analyzed in the plasma of Patient #19.
Figure 2:
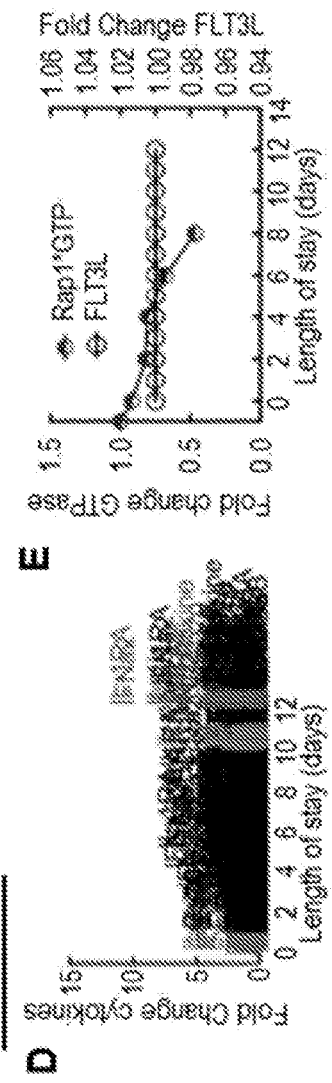
Figure 6:
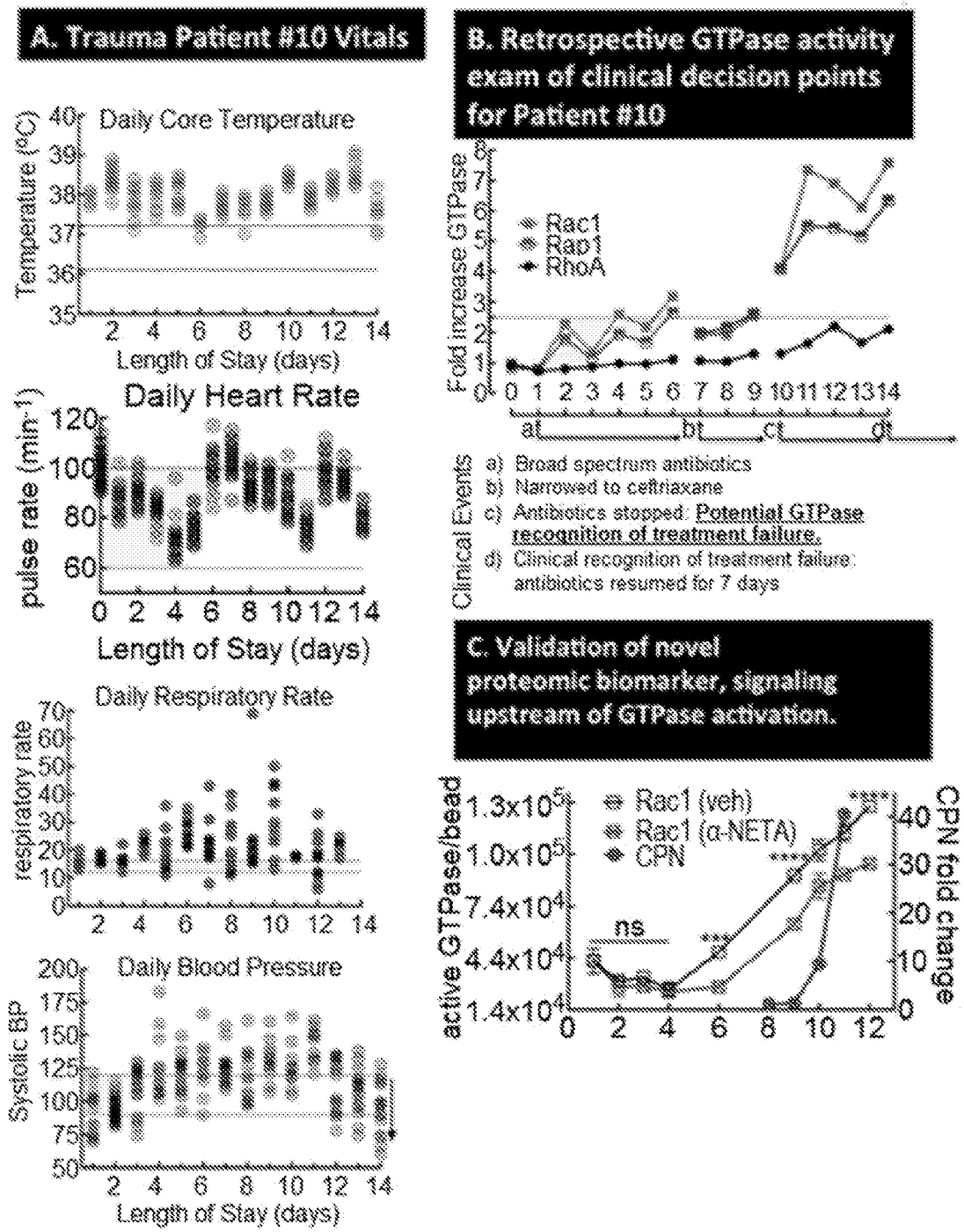
FIG. 6 shows assay validation for patient 10 which is set forth in greater detail in the example section which follows.
Figure 7:
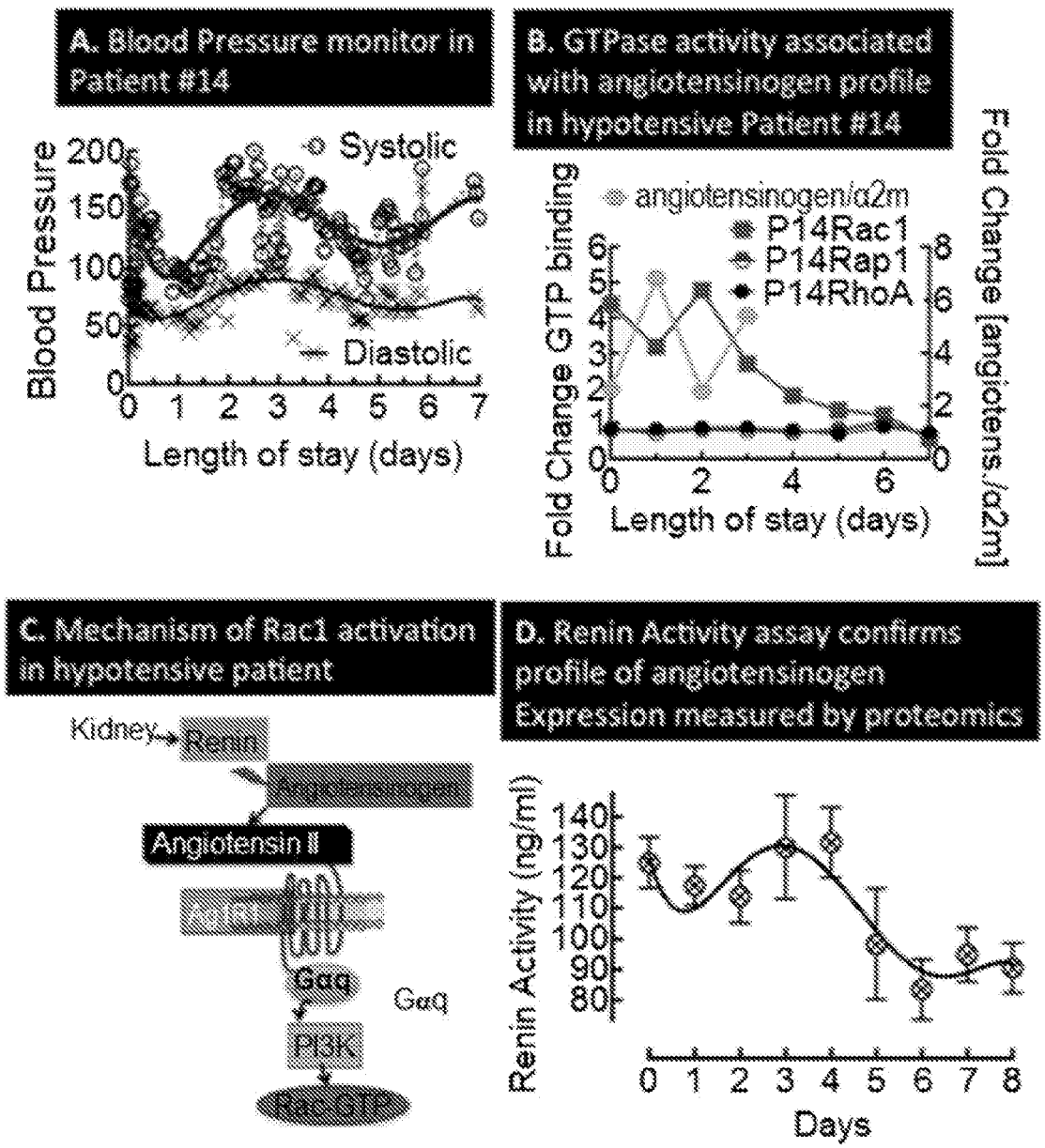
FIG. 7 shows assay validation for patient 14 which is set forth in greater detail in the example section which follows.
Figure 8:
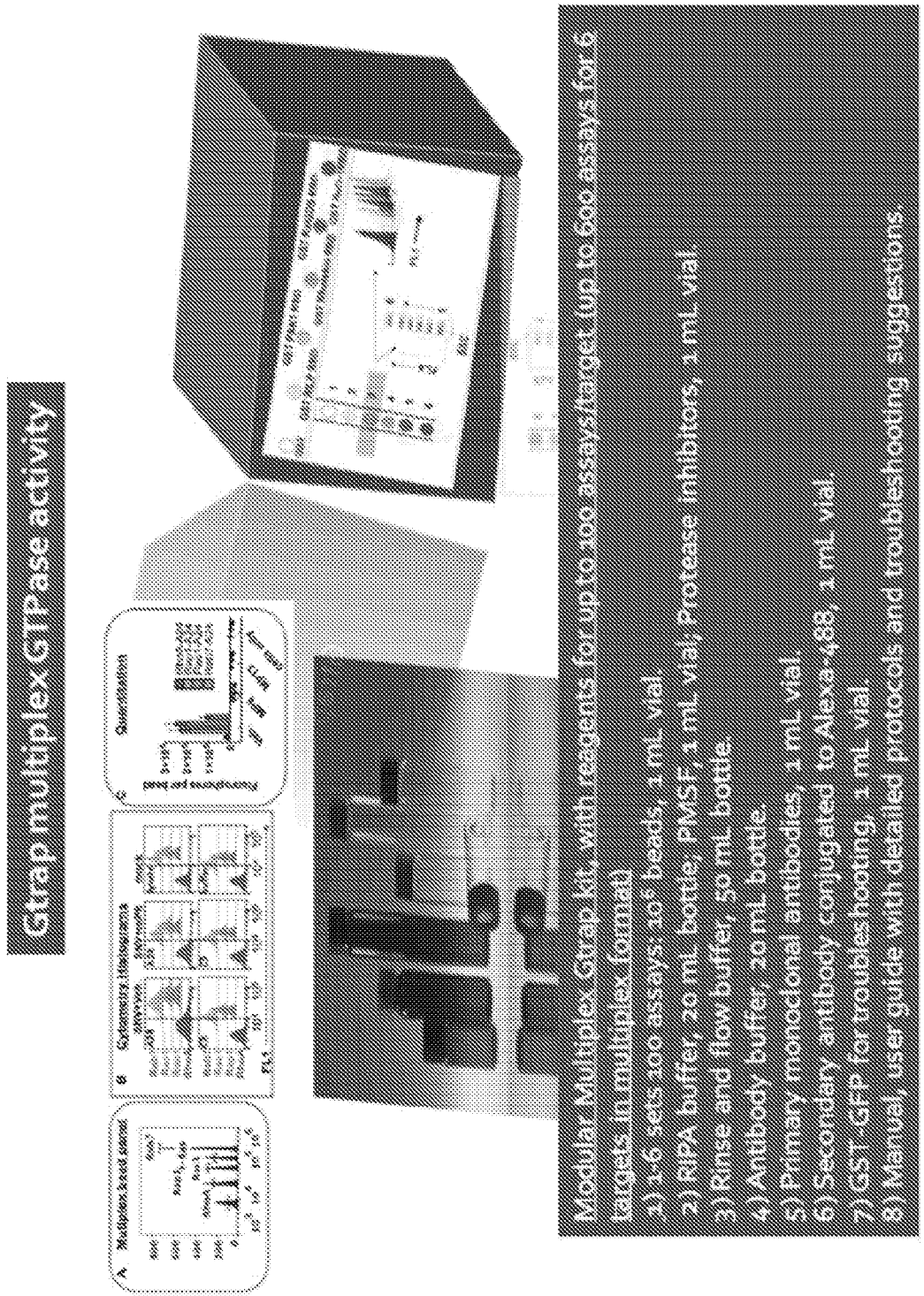
FIG. 8 shows G-Trap multiplex GTPase activity and an exemplary modular multiplex G-Trap kit for determining GTP activity.

A single analyte capture mode in FIGS. 6 and 7 hereof. FIGS. 6 and 7 show the basic principles of lateral flow assay: Zone 1 shows the sample loading component matrix. The fluid sample may be a biological fluid such as, whole blood, serum, plasma, cell lysates derived from patient leukocytes. Multiple different analytes may be detected from a single fluid sample. For our purposes the sample might be a patient sample suspected of elevated expression of Flt3-L or active GTPases such as Rap1. Zone 2 contains color beads functionalized with antibodies specific to Flt3-L or GTP effector proteins that specifically recognize GTP-bound, but not GDP bound small GTPases. The target analytes present in the sample fluid are captured by the beads, which are allowed to flow towards Zone 3 by capillary action. The analyte capture zone, comprises a single or series immobilized antibody barriers to capture bead-borne analytes. The antibody barriers might comprise anti FLT3-L or antibodies against target GTPases. A final barrier comprising antibodies not associated with targets of interest are used to define the degree of non-specific binding. To address our quantitative needs, and need for capturing tandem analytes the multiplex format disclosed in PCT publication WO 98/39657 can be used, which is incorporated by reference herein. In this embodiment a device designed with multiple branches each defining a discrete flow path downstream of a common Zone 1 as shown in FIG. 2. Using multiple barrier lines in Zone 3, As might be apparent to one of skill in the art, for a given concentration of analyte in the sample, the first barrier is likely to deplete flow through analytes and get saturated, while downstream capture zones will take increasingly longer to produce a detectable signal compared to a capture zone that is upstream from it. The propagation of analyte capture is dependent of analyte concentration. In this way the higher the analyte concentration the more capture lines are observed and vice versa. By using known standards a person of skill in the art can establish a series of calibration pattern of lines correlated to the concentration of target analytes. Such a calibration sheet might be provided with an assay kit. Exemplary lateral flow assays for use in the present invention are set forth in FIGS. 6 and 7 hereof. In addition to a lateral flow assay, a multiplex lateral flow assay as presented in FIG. 8 hereof may also be used.

The term "sepsis" is used to describe a clinical syndrome that complicates severe infection. It is characterized by the cardinal signs of inflammation (vasodilation, leukocyte accumulation, increased microvascular permeability) occurring in tissues that are remote from the infection. Systemic inflammatory response syndrome (SIRS) is an identical clinical syndrome that complicates a noninfectious insult (e.g., acute pancreatitis, pulmonary contusion). Current theories about the onset and progression of sepsis and SIRS focus on dysregulation of the inflammatory response, including the possibility that a massive and uncontrolled release of proinflammatory mediators initiates a chain of events that lead to widespread tissue injury. This response can lead to multiple organ dysfunction syndrome (MODS), which is the cause of the high mortality associated with these syndromes.

Sepsis is typically associated with a bacterial infection and is characterized by a whole-body inflammatory state (SIRS) and the presence of a known or suspected infection. The body may develop this inflammatory response by the immune system to bacteria presence in the blood, urine, lungs, skin, or other tissues. Sepsis is also referred to as "blood poisoning" or septicemia. Severe sepsis is the systemic inflammatory response, plus infection, plus the presence of at least one organ dysfunction. Septicemia (also sometimes referred to as bacteremia) refers to the presence of pathogenic organisms in the bloodstream, leading to sepsis.

An *S. aureus* infection can cause septic arthritis. Bacterial arthritis (or septic arthritis) is a rapidly progressive and highly destructive joint disease in humans. Clinical symptoms of septic arthritis include red, swollen, warm, painful and dysfunctional joints. Septic arthritis develops when bacteria spread through the bloodstream to a joint and it may also occur when the joint is directly infected with a microorganism from an injury or during surgery. The most common sites for this type of infection are the knee and hip.

In the United States, sepsis is the second-leading cause of death in non-coronary ICU patients, and the tenth-most-common cause of death overall according to data from the Centers for Disease Control and Prevention (the first being heart disease). Sepsis is common and also more dangerous in elderly, immunocompromised, and critically ill patients. It occurs in 1-2% of all hospitalizations and accounts for as much as 25% of intensive-care unit (ICU) bed utilization. It is a major cause of death in intensive-care units worldwide, with mortality rates that range from 20% for sepsis to 40% for severe sepsis to >60% for septic shock.

Septic shock is a medical emergency caused by decreased tissue perfusion and oxygen delivery as a result of severe infection and sepsis, though the microbe may be systemic or localized to a particular site. It can cause multiple organ dysfunction syndrome (formerly known as multiple organ failure) and death. Its most common victims are children, immunocompromised individuals, and the elderly, as their immune systems cannot deal with the infection as effectively as those of healthy adults. Frequently, patients suffering from septic shock are cared for in intensive care units. The mortality rate from septic shock is approximately 25%-50%. See United States Patent Application Document No. 20140162978.

Adequate management of septic patients is often complicated by delay in administering therapy after sepsis has been recognized. Every hour delay in the administration of appropriate antibiotic therapy there is associated with a significant rise in mortality.

"Sepsis" as used herein includes all of the aforementioned septic states, conditions and clinical symptoms, e.g. "sepsis" includes but is not limited to systemic inflammatory response syndrome (SIRS), septicemia, septic arthritis and septic shock.

The term "treatment of sepsis", "sepsis treatment" or "traditional treatment of sepsis" refers to a traditional treatment of sepsis including an appropriate antibiotic regimen to treat the underlying cause of the sepsis. In most instances, the causative agent is a bacterial infection (the bacteria releases lipopolysaccharide into the blood stream of the patient or subject which causes an upregulation in Rap1-GTP, which upregulation causes the upregulation in Flt3-L which causes an upregulation in Rac1). Sepsis treatments include the administration of antibiotics, initially broad spectrum antibiotics administered intravenously immediately after or as soon as possible after making a diagnosis of sepsis. After further analysis pursuant to the present invention of monitoring the levels of Flt3-L and Rap1-GTP and optionally, Rac1, the caregiver may modify the antibiotic regimen in the patient or subject. In addition to administering an antibiotic regimen to inhibit and ameliorate the bacterial infection, the patient or subject often will receive intravenous fluids and/or vasopressor medication in order to elevate blood pressure which has become too low even after the administration of intravenous fluids. In addition, other medications which may be administered to the patient or subject include one or more of low doses of corticosteroids, insulin to maintain stable blood sugar levels, immune regulators, sedatives and painkillers.

In severe sepsis and septic shock, broad-spectrum antibiotics such as a broad spectrum β-lactam antibiotic or a broad-spectrum carbapenem, or a mixture thereof, which can be used alone or combined with fluoroquinolones, macrolides, or aminoglycosides. In general, a combination of antibiotics may not be recommended for the treatment of sepsis but without shock and immunocompromised persons unless the combination is used to broaden the anti-bacterial activity. The choice of antibiotics is important in controlling sepsis and ultimately determining the survival of the patient. It is often recommended that antibiotics are commenced within an hour of making the diagnosis.

For severe sepsis and septic shock a broad spectrum antibiotic (often two such antibiotics) are administered intravenously or intravenously and orally to the patient or subject at the first indication that the patient or subject has sepsis. The antibiotics may include, for example a β-lactam antibiotic with broad coverage such as broad spectrum penicillin derivatives (penams) amoxicillin and ampicillin, carboxylpenicillins (e.g. carbenicillin and ticarcillin), cephalosporins (cephems) such as cefixime, cefotaxime, cefpodoxime, ceftazidime, ceftriaxone, cefdinir, ceftaroline fosnir all of which are broad spectrum, monobactams (e.g. aztreonam, tigemonam, carumonam and nocardicin A) and carbapenems (e.g. doripenem, faropenem, imipenem, meropenem, ertapenem, panipenim, razupenem, tebipenem, thienamycin or cilastatin/imipenem) each of which is used alone or in combination or each is used in combination with a fluoroqunoline (e.g. ciprofloxacin, levofloxacin, fleroxacin, lomefloxacin, nadifloxacin, norfloxacin, ofloxacin, perfloxacin, rufloxacin, balofloxacin, grepafloxacin, pazufloxacin, sparfloxacin, temafloxacin, garenoxacin, gatifloxacin, gemifloxacin, moxifloxacin, clinafloxacin, sitafloxacin, prulifloxacin, besifloxacin, delafloxacin and ozenoxacin, among others), a macrolide (e.g. (e.g., azithromycin, clarithromycin, erythromycin, fiaxomycin, telithromycin, carbomycin A, josamycin A, kitasamycin, midecamycin/midecamycin acetate, oleandomycin, solithromycin, spiramycin, troleandomycin and roxithromycin, related ketolides including telithromycin, cethromycin and solithromycin).

Principally, sepsis treatment is established to provide appropriate and effective antibiotics as early as possible after diagnosis of sepsis. In addition, antimicrobials may be added to the antibiotics regimen in order to be effective against the pathogens causing septic shock intravenously within the first hour after severe sepsis or septic shock is recognized. Antimicrobials, when used as optional agents, should be chosen that cover all the likely causative pathogens—nearly always including bacteria, but sometimes also fungi and/or viruses. Antibiotics must be selected according to the patient's unique clinical picture (symptoms, signs, indwelling devices, neutropenia, gut integrity, etc.), and also guided by local patterns of infection and resistance (e.g., high community rates of MRSA; high hospital rates of fluoroquinolone-resistant *Pseudomonas*, etc.) This complex process cannot be protocolized and depends on the judgement of the physician with information established by the monitoring processes of the present invention.

After appropriately broad antibiotic therapy has begun for patients with severe sepsis or septic shock, consideration should be given throughout the patient's clinical course to reducing antibiotic therapy to the minimum drugs and doses necessary based upon the monitoring methods according to the present invention which are described herein. The features of this approach are to review the antibiotic/antimicrobial regimen daily, and de-escalate therapy (eliminate unnecessary antibiotics; change to narrow-spectrum antibiotics) whenever appropriate based upon a clear indication from that infection in a patient or subject is subsiding. In many instances it is not enough that the infection is not getting worse—the infection must be falling.

In certain instances it may be appropriate to consider using procalcitonin to help gain confidence in stopping empiric antibiotics in patients who appeared to have severe sepsis or septic shock at first, but now have a lower suspicion for infection because Rap1-GTP and Flt3-L levels (optionally confirmed by Rac1 levels) have fallen. Low procalcitonin levels reduce the likelihood of bacterial infection, albeit imperfectly.

When to Use Combination Antibiotic Therapy for Severe Sepsis/Septic Shock

Use of combination therapy (multiple drugs active against the same organisms, through different mechanisms of action as described herein) when appropriate, but for only a limited time (3-7 days, often no more than 3-5 days). Certain combination therapy is recommended for patients with septic shock or severe sepsis and Neutropenia; Multi-drug resistant bacteria like *Pseudomonas, Acinetobacter*, et al.; *Pseudomonas aeruginosa* bacteremia causing septic shock and respiratory failure; use of an extended-spectrum beta-lactam and either a fluoroquinolone or aminoglycoside, as described above and for *Streptococcus pneumoniae* with bacteremia and septic shock, combine a beta-lactam, especially broad spectrum and a macrolide. Other situation may call for combination therapy including the use of carbapenems, colistin, rifampin, or other drugs (e.g., settings in which highly resistant organisms are prevalent); evidence is largely absent to guide these decisions and no guidelines can advise on all such clinical situations. In general, when using combination therapy is used, eliminate one or more of the antimicrobials being used based upon the monitoring profile of the present invention wherein Rap1-GTP and Flt3-L (optionally confirmed by Rac1) levels are falling. Antibiotic use should be narrowed as soon as data are available.

How Long to Treat Severe Sepsis/Septic Shock With Antibiotics?

Most infections in patients with severe sepsis or septic shock are treated with antibiotics for about 7-10 days total. Longer treatment might be appropriate for patients who are responding slowly; have abscesses, empyema, or other infectious foci which are not amenable to drainage; have *Staphylococcus aureus* bacteremia; have unusual infections (e.g., fungal or viral infections) and/or have immune deficiencies (e.g., neutropenia).

In cases where the infectious agent is a virus or fungus, antiviral/antifungal therapy in the unusual patients with severe sepsis or septic shock caused by viral/fungal infections. These infections, though less common than bacterial infections which cause sepsis, may be diagnosed and monitored by the methods described herein.

Sepsis treatments include the administration of antibiotics and/or antimicrobial agents, often initially broad spectrum antibiotics administered intravenously immediately after or as soon as possible after making a diagnosis of sepsis. After further analysis pursuant to the present invention of monitoring the levels of Flt3-L and Rap1-GTP and optionally, Rac1, the caregiver may modify the antibiotic/antimicrobial regimen in the patient or subject. In addition to administering an antibiotic regimen to inhibit and ameliorate the bacterial infection, the patient or subject often will receive intravenous fluids and/or vasopressor medication in order to elevate blood pressure which has become too low even after the administration of intravenous fluids. In addition, other medications which may be administered to the patient or subject include one or more of low doses of corticosteroids, insulin to maintain stable blood sugar levels, immune regulators, sedatives and painkillers.

The term "compound" is used herein to describe any specific compound or bioactive agent disclosed herein, including any and all stereoisomers (including diastereomers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein.

A "control" as used herein may be a positive or negative control as known in the art and can refer to a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data from one or more control subjects that is stored in a reference database. The control may be a subject who is similar to the test subject (for instance, may be of the same gender, same race, same general age and/or same general health) but who is known to not have a fibrotic disease. As can be appreciated by a skilled artisan, the methods of the invention can also be modified to compare a test subject to a control subject who is similar to the test subject (for instance, may be of the same gender, same race, same general age and/or same general health) but who is known to express symptoms of a disease.

In this embodiment, a diagnosis of a disease or staging of a disease can be made by determining whether protein or gene expression levels as described herein are statistically similar between the test and control subjects.

Purely by way of example, comparing measured levels of an infection-associated biomarker (i.e., Rap1-GTP and Flt3-L and optionally, Rac1) in a sample to corresponding control levels (i.e., a standard), to control levels determined in a healthy control subject (including the patient or subject who is suspected of having a bacterial infection and/or sepsis), and determining that a subject suffers from sepsis or that a subject's sepsis is progressing, can include determinations based on comparative level differences of about between about 5-10%, or about 10-15%, or about 15-20%, or about 20-25%, or about 25-30%, or about 30-35%, or about 35-40%, or about 40-45%, or about 45-50%, or about 50-55%, or about 55-60%, or about 60-65%, or about 65-70%, or about 70-75%, or about 75-80%, or about 80-85%, or about 85-90%, or about 90-95%, or about 95-100%, or about 100-110%, or about 110-120%, or about 120-130%, or about 130-140%, or about 140-150%, or about 150-160%, or about 160-170%, or about 170-180%, or about 180-190%, or 190-200%, or 200-210%, or 210-220%, or 220-230%, or 230-240%, or 240-250%, or 250-260%, or about 260-270%, or about 270-280%, or about 280-290%, or about 290-300%, or differences of about between about ±50% to about ±0.5%, or about: ±45% to about ±1%, or about #40% to about ±: 1.5%, or about: 35% to about ±2.0%, or about ±30% to about: ±2.5%, or about ±25% to about ±3.0%, or about ±20% to about ±3.5%, or about ±15% to about +4.0%, or about ±10% to about ±5.0%, or about ±9% to about ±1.0%, or about ±8% to about ±2%, or about ±7% to about ±3%, or about ±6% to about =5%, or about ±5%, or about ±4.5%, or about ±4.0%, or about ±3.5%, or about ±3.0%, or about ±2.5%, or about =2.0%, or about ±1.5%, or about ±1.0%. In embodiments, the level of Rap1-GTP and Flt-3L and optionally Rac1-GTP at which sepsis diagnosis is first made in a patient is often at least 1.5-2 times up to 8-10 times or more (e.g. 15 or more) of the baseline values for each of these biomarkers in a control setting (e.g. patient free from sepsis or a population of patients free from sepsis).

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

A "biological sample" can be a tissue sample or a cell sample, and most preferably is a plasma or blood sample, but may also include a lysate of white blood cells obtained from a subject to be tested. In embodiments the biological sample is whole blood, plasma, serum, white blood cells or a white blood cell fraction or blood or lysate or leukocytes or other biological sample such as urine, saliva, sputum and the like. In embodiments, Flt3-L is identified from blood or serum samples and Rap1-GTP and/or Rac1-GTP are identified from white blood cell fragments or lysates of leukocytes obtained from the patient.

As used herein, the terms "nucleotide" and "polynucleotide" refer respectively to monomeric or polymeric form of nucleotides of any length, either ribonucleotides or deoxynucleotides, and include both double- and single-stranded DNA and RNA. A nucleotide or polynucleotide may include nucleotide sequences having different functions, such as coding regions, and non-coding regions such as regulatory sequences (e.g., promoters or transcriptional terminators). A polynucleotide can be obtained directly from a natural source, or can be prepared with the aid of recombinant, enzymatic, or chemical techniques. A nucleotide or polynucleotide can be linear or circular in topology. A nucleotide or polynucleotide can be, for example, a portion of a vector, such as an expression or cloning vector, or a fragment.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e g., dimers, tetramers). Thus, the terms peptide, oligopeptide, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

A "ligand" can be any natural or synthetic moiety, including but not limited to a small molecule, an antibody, a nucleic acid, an amino acid, a protein (e.g. an enzyme) or a hormone that binds to a cell, preferably at a receptor (binding site) located on the surface of the cell. The term "ligand" therefore includes any targeting active species (compound or moiety, e.g. antigen) which binds to a moiety (preferably a receptor) on, in or associated with a cell. In some embodiments, a ligand is a peptide, a polypeptide including an antibody or antibody fragment, an aptamer, or a carbohydrate, among other species which bind to a targeted cell.

"Binding site" as used herein is not limited to receptor protein surface areas that interact directly with ligands, but also includes any atomic sequence, whether or not on the surface of a receptor, that is implicated (by affecting conformation or otherwise) in ligand binding. A purely illustrative list of binding sites include those targeted by detector antibodies which are specific to the specific antibodies, and those targeted by specific antibodies, as illustrated by the antibodies described in the Examples herein and as otherwise identifiable by techniques which are well-known to those of ordinary skill in the art.

Diagnostic methods of the present invention utilize an antibody, preferably, a monocolonal or polyclonal antibody or a fusion protein such as a GST fusion protein, capable of specifically binding to a biomarker as described herein or active fragments thereof. The method of utilizing an antibody to measure the levels of protein allows for non-invasive diagnosis of the pathological states of sepsis. In a preferred embodiment of the present invention, the antibody is a mouse or rabbit monoclonal or polyclonal antibody or may be a human antibody or is humanized. Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

"Fluorophores" small molecule fluors and proteinaceous fluors (e.g. green fluorescent proteins and derivatives thereof). Useful fluorophores include, but are not limited to, 1,1-diethyl-2,2'-cyanine iodide, 1,2-diphenylacetylene, 1,4-diphenylbutadiene, 1,6-Diphenylhexatriene, 2-Methylbenzoxazole, 2,5-Diphenyloxazole (PPO), 4-(dicyanomethylene)-2-methyl-6-(p-dimethylaminostyryl)-4H-pyran (DCM), 4-Dimethylamino-4'-nitrostilbene, 4',6-Diamidino-2-phenylindole (DAPI), 5-ROX, 7-AAD, 7-Benzylamino-4-nitrobenz-2-oxa-1,3-diazole, 7-Methoxycoumarin-4-acetic acid, 9,10-Bis(phenylethynyl) anthracene, 9,10-Diphenylanthracene, Acridine Orange, Acridine yellow, Adenine, Allophycocyanin (APC), AMCA, AmCyan, Anthracene, Anthraquinone, APC, Auramine O, Azobenzene, Benzene, Benzoquinone, Beta-carotene, Bilirubin, Biphenyl, BO-PRO-1, BOBO-1, BODIPY FL, Calcium Green-1, Cascade Blue.™., Cascade Yellow.™., Chlorophyll a, Chlorophyll b, Chromomycin, Coumarin, Coumarin 1, Coumarin 30, Coumarin 314, Coumarin 343, Coumarin 6, Cresyl violet perchlorate, Cryptocyanine, Crystal violet, Cy2, Cy3, Cy3.5, Cy5, Cy5.5, Cy7, Cytosine, DA, Dansyl glycine, DAPI, DiI, DIO, DiOCn, Diprotonated-tetraphenylporphyrin, DsRed, EDANS, Eosin, Erythrosin, Ethidium Monoazide, Ethyl p-dimethylaminobenzoate, FAM, Ferrocene, FI, Fluo-3, Fluo-4, Fluorescein, Fluorescein isothiocyanate (FITC), Fura-2, Guanine, HcRed, Hematin, Histidine, Hoechst, Hoechst 33258, Hoechst 33342, IAEDANS, Indo-1, Indocarbocyanine (C3) dye, Indodicarbocyanine (C5) dye, Indotricarbocyanine (C7) dye, LC Red 640, LC Red 705, Lucifer yellow, LysoSensor Yellow/Blue, Magnesium octaethylporphyrin, Magnesium octaethylporphyrin (MgOEP), Magnesium phthalocyanine (MgPc), Magnesium tetramesitylporphyrin (MgTMP), Magnesium tetraphenylporphyrin (MgTPP), Malachite green, Marina Blue.RTM., Merocyanine 540, Methyl-coumarin, MitoTracker Red, N,N'-Difluoroboryl-1,9-dimethyl-5-(4-iodophenyl)-dipyrrin, N,N'-Difluoroboryl-1,9-dimethyl-5-[(4-(2-trimethylsilylethynyl), N,N'-Difluoroboryl-1,9-dimethyl-5-phenydipyrrin, Naphthalene, Nile Blue, Nile Red, Octaethylporphyrin, Oregon green, Oxacarbocyanine (C3) dye, Oxadicarbocyanine (C5) dye, Oxatricarbocyanine (C7) dye, Oxazine 1, Oxazine 170, p-Quaterphenyl, p-Terphenyl, Pacific Blue®, Peridinin chlorophyll protein complex (PerCP), Perylene, Phenol, Phenylalanine, Phthalocyanine (Pc), Pinacyanol iodide, Piroxicam, POPOP, Porphin, Proflavin, Propidium iodide, Pyrene, Pyronin Y, Pyrrole, Quinine sulfate, R-Phycoerythrin (PE), Rhodamine, Rhodamine 123, Rhodamine 6G, Riboflavin, Rose bengal, SNARF®, Squarylium dye III, Stains-all, Stilbene, Sulforhodamine 101, SYTOX Blue, TAMRA, Tetra-t-butylazaporphine, Tetra-t-butylnaphthalocyanine, Tetrakis(2,6-dichlorophenyl) porphyrin, Tetrakis(o-aminophenyl) porphyrin, Tetramesitylporphyrin (TMP), tetramethylrhodamine, Tetraphenylporphyrin (TPP), Texas Red® (TR), Thiacarbocyanine (C3) dye, Thiadicarbocyanine (C5) dye, Thiatricarbocyanine (C7) dye, Thiazole Orange, Thymine, TO-PRO.RTM.-3, Toluene, TOTO-3, TR, Tris(2,2'-bipyridyl) ruthenium (II), TRITC, TRP. Tryptophan, Tyrosine, Uracil, Vitamin B12, YO-PRO-1, YOYO-1, Zinc octaethylporphyrin (ZnOEP), Zinc phthalocyanine (ZnPc), Zinc tetramesitylporphyrin (ZnTMP), Zinc tetramesitylporphyrin radical cation, and Zinc tetraphenylporphyrin (ZnTPP). Suitable optical dyes are described in the 1996 Molecular Probes Handbook by Richard P. Haugland, hereby expressly incorporated by reference.

In some embodiments, one of the fluorescent dyes may be an Alexa Fluor® dye, including Alexa Fluor®, Alexa Fluor® 405, Alexa Fluor Alexa Fluor® 430, Alexa Fluor Alexa Fluor® 488, Alexa Fluor®500, Alexa Fluor®514, Alexa Fluor®532, Alexa Fluor®546, Alexa Fluor®555, Alexa Fluor®568, Alexa Fluor® 594, Alexa Fluor® 610, Alexa Fluor®633, Alexa Fluor® 647, Alexa Fluor®660, Alexa Fluor®680, Alexa Fluor®700, and Alexa Fluor®750 (Life Technologies Corporation Carlsbad, California).

One of the fluorescent dye may be a tandem fluorophore conjugate, including Cy5-PE, Cy5.5-PE, Cy7-PE, Cy5.5-APC, Cy7-APC, Cy5.5-PerCP, Alexa Fluor®610-PE, Alexa Fluor® 700-APC, and Texas Red-PE. Tandem conjugates are less stable than monomeric fluorophores, so comparing a detection reagent labeled with a tandem conjugate to reference solutions may yield MESF calibration constants with less precision than if a monomeric fluorophore had been used.

The fluorophores may be a fluorescent protein such as green fluorescent protein (GFP; Chalfie, et al., Science 263 (5148): 802-805 (Feb. 11, 1994); and EGFP; Clontech—Genbank Accession Number U55762), blue fluorescent protein (BFP; Quantum Biotechnologies, Inc. Montreal Canada; Stauber, R. H. Biotechniques 24 (3): 462-471 (1998); Heim, R. and Tsien, R. Y. Curr. Biol. 6:178-182 (1996)), cyan fluorescent protein (CFP), and enhanced yellow fluorescent protein (EYFP; Clontech Laboratories, Inc., Palo Alto, California). In some embodiments, the fluorescent dye is dTomato, FlAsH, mBanana, mCherry, mHoneydew, mOrange, mPlum, mStrawberry, mTangerine, ReAsH, Sapphire, mKO, mCitrine, Cerulean, Ypet, tdTomato, Emerald, or T-Sapphire (Shaner et al., Nature Methods, 2 (12): 905-9. (2005)).

The fluorophores may be a fluorescent dye in the form of a fluorescent semiconductor nanocrystal particle, or quantum dot, including Qdot®525 nanocrystals, Qdot@565 nanocrystals, Qdot@585 nanocrystals, Qdot®605 nanocrystals, Qdot®655 nanocrystals, Qdot®705 nanocrystals, Qdot®800 nanocrystals (Life Technologies Corporation, Carlsbad, California). In some embodiments, the fluorescent dye may be an upconversion nanocrystal, as described in Wang et al., Chem. Soc. Rev., 38:976-989 (2009).

The fluorescent molecules (fluorophores) may be conjugated with antibodies or other detection reagents, and associated with components of a sample that is analyzed by the instrument. Fluorophores can be activated by light from the instrument and re-emit light of a different wavelength. Since antibodies bind to antigens on the cells, the amount of light detected from the fluorophores is related to the number of antigens associated with the cell passing through the beam. In another embodiment of the invention, a fluorescently-labeled DNA oligonucleotide can be associated with the genomic DNA of a cell, and the amount of light detected from the fluorophores is related to the number of copies of the oligonucleotide that have hybridized to complimentary regions in the genome. Any specific set of fluorescently tagged detection reagents in any embodiment can depend on the types of experimental samples to be studied. See United States Patent Application Document No. 20130109050. As further explained in United States Patent Application Document No. 20130109050, "[s]everal fluorescent detection reagents can be used simultaneously, so measurements made as one cell passes through the laser beam consist of scattered light intensities as well as light intensities from each of the fluorophores. Thus, the characterization of a single cell can consist of a set of measured light intensities that may be represented as a coordinate position in a multidimensional space. Considering only the light from the fluorophores, there is one coordinate axis corresponding to each of the fluorescently tagged detection reagents. The number of coordinate axes (the dimension of the space) is the number of fluorophores used. Modern flow cytometers can measure several colors associated with different fluorophores and thousands of cells per second. Thus, the data from one subject can be described by a collection of measurements related to the number of antigens for each of (typically) many thousands of individual cells. See U.S. Pat. Nos. 7,381,535 and 7,393,656 for examples of flow cytometry methods and applications, which are hereby incorporated by reference in their entirety."

Those of ordinary skill in the art know how to select a second fluorophore that has a wavelength (color) which is different from that of the first fluorophore as required in various embodiments of the methods described and claimed herein.

The present invention therefore provides rapid, immune flow chromatographic and multiplex flow-cytometry assays to quickly assess sepsis-related biomarker (Rap1-GTP and Flt3-L) status in a single sample. In particular, the present invention relates to the use of immune flow chromatographic and multiplex flow cytometry-compatible, bead-based binding assays for rapidly monitoring the activation status of Rap1-GTP and Flt3-L biomarkers in cell lysates. The present inventors have demonstrated proof-of-principle in ICU patients.

The invention is illustrated further in the following non-limiting examples.

Examples and Preferred Embodiments (Second Set of References)

Overview

Sepsis accounts for 33% of deaths in hospitalized patients each year. Sepsis is the most expensive disease state in acute care hospitals in the U.S., and it exerts considerable costs for the Military Health System and the Veterans Administration for both critical care and long-term care. With 1.37 million active duty service members and 5.4 million retirees, infectious disease-treatment while minimizing antibiotic use is a high priority area for the Military Health System. Many sepsis survivors experience long-term effects caused by sepsis, called post-sepsis syndrome. The results can be physical and evident, such as amputations, or obscured such as chronic pain and fatigue or cognitive changes; or mental, such as post-traumatic stress disorder.[1-3] Increased mortality and delayed antibiotic treatment are directly linked. Because infection is frequently not confirmed before antibiotic therapy, the attendant overuse of antibiotics contributes to antibiotic resistance, which is a severe and increasing threat to public health and military operations. Currently, there is no definitive, Food and Drug Administration (FDA)-approved diagnostic test to confirm bacterial infection with the rapidity that is required for life-or-death clinical decision-making nor for assessing antibiotic efficacy. Existing tools rely on molecular diagnostics development designed to detect and identify specific pathogens directly in blood. Multiplexed PCR methods, such as SeptiFast (Roche, Diagnostics GmbH), Hybcell® Pathogens (Anagnostics Bio-analysis GmbH), and the PCR-ESI-MS method, IRIDICA (Abbott Molecular) are useful companion rapid diagnostics (4-6 hr, >90% sensitivity and specificity) for recognized blood infections. However, poor sensitivity (10-40%) for all patients with otherwise undetected bloodstream infections is a significant drawback. Also, these tools are not practical for a low resource environment or remote theatre operations. Serum procalcitonin measurement is an approved sepsis test, though non-specific because procalcitonin is also typically elevated in non-septic trauma patients-a reason for continued interest in identifying novel, markers of sepsis.

A critical, long-felt and unmet need in sepsis treatment is the lack of specific diagnostic biomarkers to determine whether a patient is likely to benefit from antibiotic treatment and to tailor the duration of antibiotic use accordingly. The present invention is thus directed to identifying biomarkers which can enable effective treatment and management of sepsis treatment in an effort to effect favorable treatment of patients and to reduce the likely overuse of antibiotics such that resistance to a particular antibiotics regimen. Thus, the present invention represents a clinical decision support tool for sepsis that can be used to distinguish sterile inflammation from infection.

Several factors cause acute elevation of white blood cell (WBC) counts due to bone marrow response to infection, or sterile inflammation (due to injury and stress; common among warfighters, drug response, cancer, etc.). Thus, a change in WBC counts is not a specific or necessarily reliable indicator of infection. The host inflammatory responses to infection include numerous cytokines, chemokines, lipid mediators, and reactive oxygen species. So far ~approximately 180 or more distinct potential biomarkers of sepsis are known.[5,6] The high number of targets has limited their prognostic value. Small GTPases represent points of signaling convergence as well as relay switches that disseminate divergent signaling associated with immunological host responses to infection.[7,8] The novel approach of the present invention exploits the pathophysiological role of small GTPases in early sepsis that is driven by host immune response to infection. Of these, Rap1 is needed for integrin-mediated cell adhesion; whereas RhoA and Rac1 are central to cytoskeletal remodeling during chemotaxis and phagocytosis. A fourth GTPase, Arf6, which regulates the intercellular cell junctions is prone to inducing catastrophic vascular permeability if persistently activated during sepsis. The inventors have developed a GTPase effector trap flow cytometry assay (G-Trap)[9] to measure GTPase activity downstream of cellular activation rapidly. In proof of principle retrospective studies of longitudinal samples from trauma patients, who developed an infection during hospitalization, the inventors have shown that blood plasma-borne agonists that are released in the circulation of trauma patients, at the onset of bacterial infection stimulate GTP binding to small GTPases.

Materials and Methods

Figure 3:
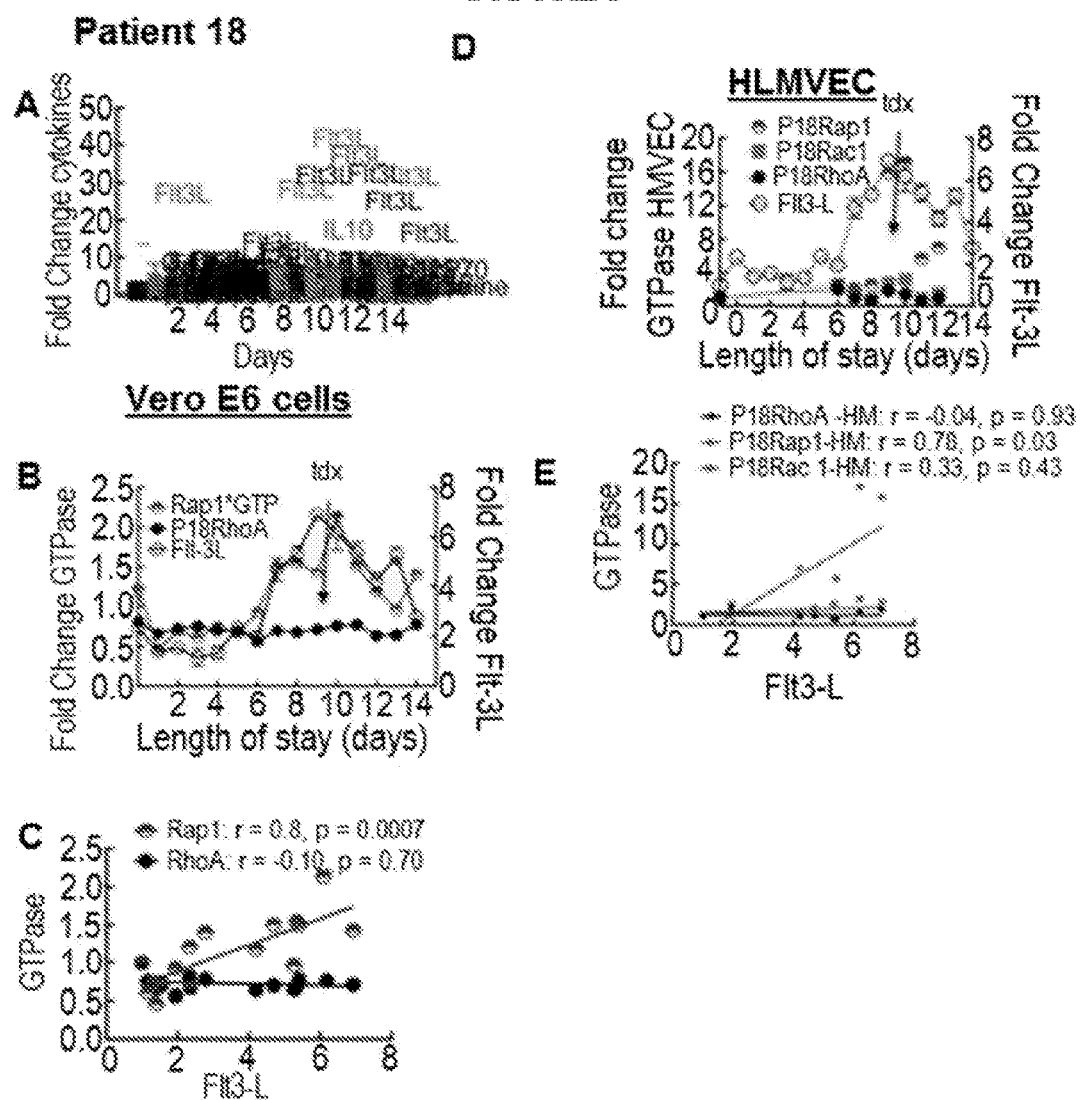
FIG. 3 shows the results for Patient #18. A. 50 year old man admitted after being hit and run over by a car. Severe injuries included left and right upper lobe pulmonary contusion, rib and vertebrate fractures. ICU length of stay (LOS) was 16 days. On post-injury day 1, he underwent operative open reduction and internal fixation of a right medial malleolus fracture and intramedullary nail fixation of a left femur fracture. On post-injury day 3, he underwent operative plating of the sternal fracture, video assisted thoracoscopic drainage of left hemothorax, and plating of left comminuted rib fractures. He received 2 units of packed RBCs during the operation. Due to requirement for prolonged mechanical ventilation, he underwent percutaneous tracheostomy on post-injury day 7. The patient remained febrile during the second week of admission, with the diagnosis of ventilator associated pneumonia (VAP) confirmed on post-injury day 9. The organism was methicillin sensitive Staph aureus (MSSA). At this time, blood cultures were also positive for Gram-positive organisms. Empiric antibiotic coverage (Vancomycin, Zosyn) was initiated at this time pending complete identity and specificity of the organisms. On post-injury day 11, he developed atrial fibrillation with rapid ventricular response requiring beta blockade and eventual treatment with amiodarone with conversion to sinus rhythm. Additional blood cultures drawn on post-injury day 13 and 15 were positive for Staph epidermidis. The patient received a complete two-week course of Vancomycin ending on post-injury day 25. The patient recovered and was transferred to a rehabilitation center on post-injury day 25. A. Patient #18's serial plasma samples were analyzed for cytokine expression shows predominant expression of Flt3-L. B. GTP binding to Rap1 and RhoA (in Vero E6 cells), superimposed with Flt3-L expression. C. Spear rank correlation indicates positive correlation between Rap1-GTP and Flt3-L expression. D. G-Trap assay of active Rap1, Rac1 and RhoA using endothelial cells. E. Positive correlation between GTP binding to Rap1 and upregulation of Flt3-L.
Figure 4:
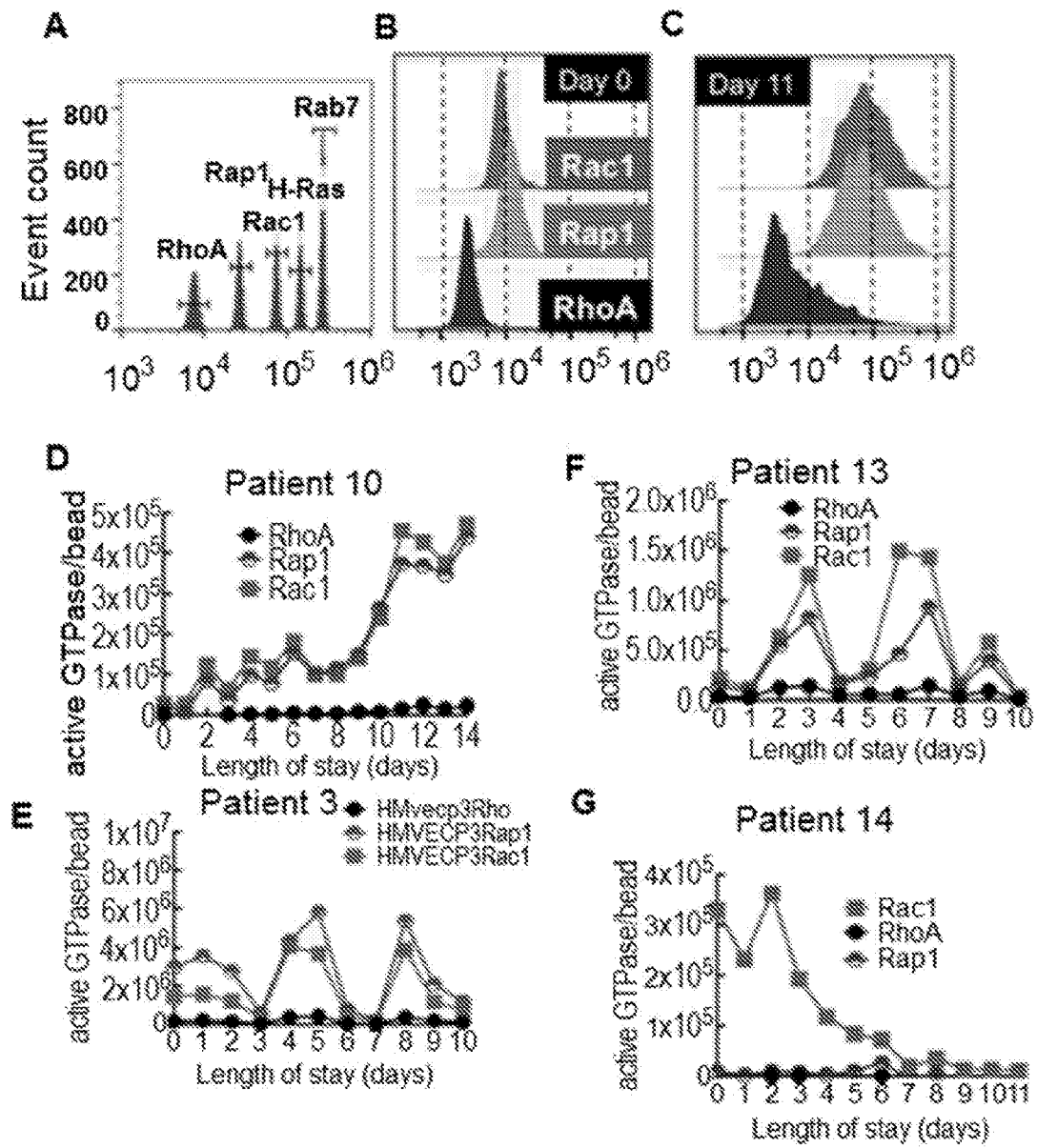
FIG. 4 G-Trap data readout, showing: A. Histograms of Cyto-Plex™ beads coded with discrete levels of 700 nm fluorescence beads for target GTPases. B&C. Flow cytometry histograms associated with GTPase activity in cell lysates exposed to blood plasma drawn from Patient #10 shown in FIG. 4D on day 0 (pre-infection) and 11 (post infection). D. Quantitative analysis of GTP binding to cytoplex beads in cell lysates treated with plasma drawn from Patient #10: a 53-year-old man was admitted after being crushed by a car. On day 2 a bacterial infection was suspected, thus a sputum culture was ordered and the patient was treated with broad-spectrum antibiotics including vancomycin and piperacillin/tazobactam. Patient ventilator settings showed increasing trends as indicated by increasing pattern of respiratory rates. Patient's blood pressure trended upwards. On day 7, sputum-culture sent on day #2 was determined to be positive for *Haemophilus influenzae* and antibiotics were changed to 3 days of ceftriaxone (days 7-9). On day 11, the patient displayed respiratory distress, and developed high fever, his clinical condition worsened around day 13/14. Ceftriaxone was started again on day 14 and lasted for 7 days resulting in patient recovery. The onset of infection was sensitively detected by an increase in GTP binding to Rap1 and Rac1. While the increase in GTPase activity was notable, the increase was however statistically insignificant for the duration of antibiotic treatment on days 2-9. After termination of antibiotic treatment, GTPAse activity increased significantly from day 10 to 14. E. Quantitative analysis of GTPase activity induced by Patient #3 plasma (see FIG. 2A-C). F. Quantitative analysis of GTPase activity induced by Patient #13 plasma. 77 year old woman admitted after fall down stairs. Injuries include left clavicle fracture, left 3-6 rib fractures, subarachnoid hemorrhage, right temporal and frontal contusion, right subdural hematoma, pneumocephalus, temporal skull fracture. ICU LOS was 13 days. Disenrolled at family request after 10 days. Developed suspected VAP on hospital day 6. Sputum culture positive for MRSA. Treated with vancomycin for approximately 10 days. G Quantitative analysis of GTPase activity induced by Patient #14 plasma; a 53-year-old man admitted with no injuries after a low-speed car collision. The patient was suspected to be septic on arrival with community-acquired pneumonia and tested positive for *S. pneumonia* on sputum culture from admission and developed gastric perforation of unclear etiology on hospital day 5 (missed injury versus stress ulcer) requiring laparotomy. Signs of sepsis present throughout ICU stay. Number of enrolled days after day zero: 11. Disenrolled due to inability to draw labs. ICU stay was 17 days in total.

As shown in FIGS. 2-4, the inventors use flow cytometry multiplex beads that are functionalized with signaling effector molecules of target GTP bound small GTPases to determine changes in the concentration of active GTPases in the blood plasma of trauma patients before and after a clinically diagnosed infection (FIGS. 6&7). In this setting, the beads capture GTP-bound GTPases in lysates of cells that were challenged with plasma samples of study subjects and then quantitatively analyzed on a flow cytometer.[9]

Significance and Uniqueness of the Proposed Effort

Figure 10:
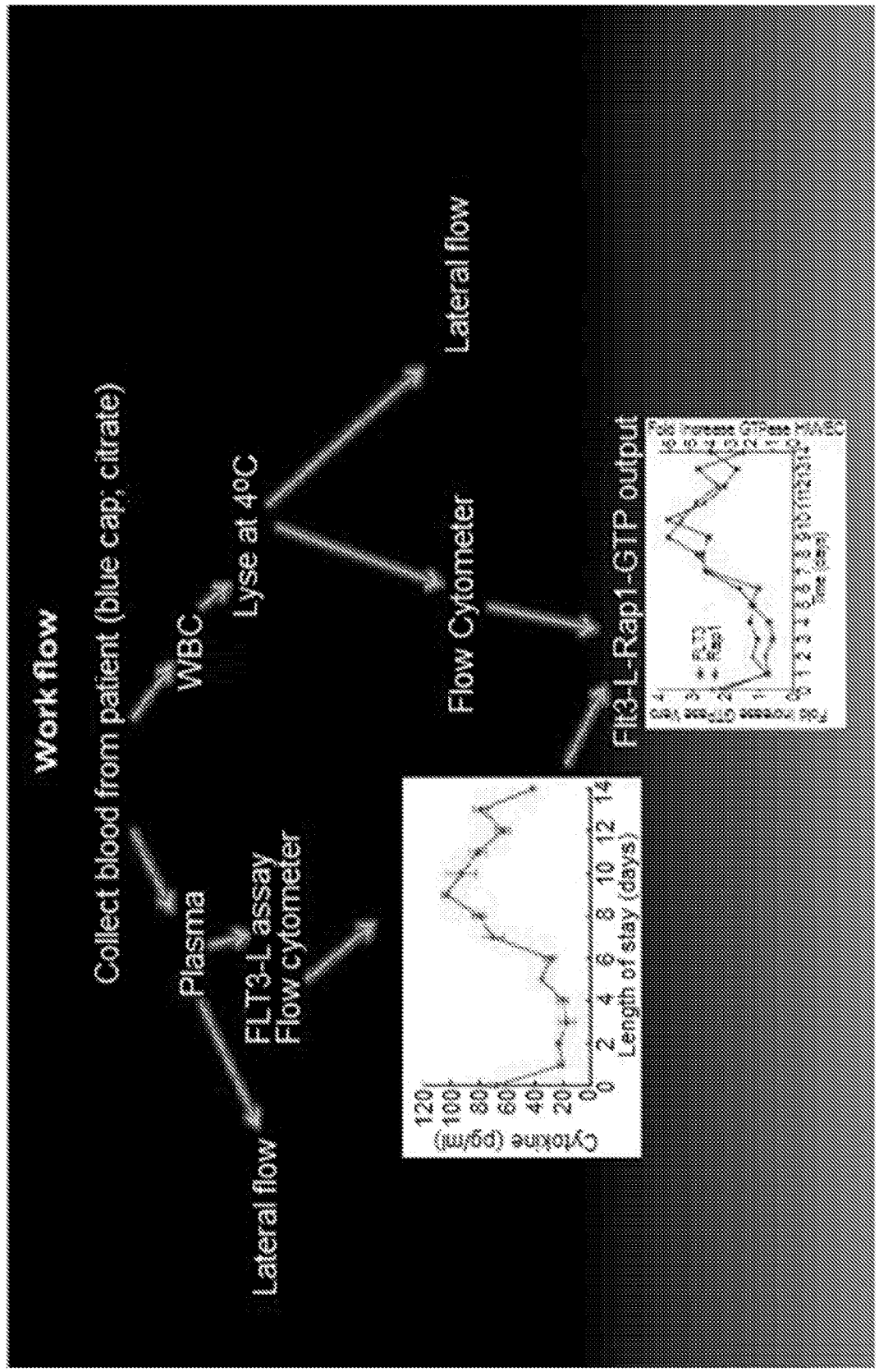
FIG. 10 shows the work flow for analysis of FLT3-L and Rap1·GTP in (left) a cytokinase assay flow cytometer (for FLT3-1) and (right) a GTPase multiplex assay (which is used to measure Rap1·GTP and optionally Rac1). Evidence of sepsis (bacterial infection) is presented when FLT3-1 and Rap1·GTP and optionally Rac1 biomarkers increase over time in the patient as evidenced by measurements obtained from the biological samples (white blood cells or lysates of same in G-Trap assay, plasma or serum in the case of cytokine assay and analysis of those measurements.
Figure 11:
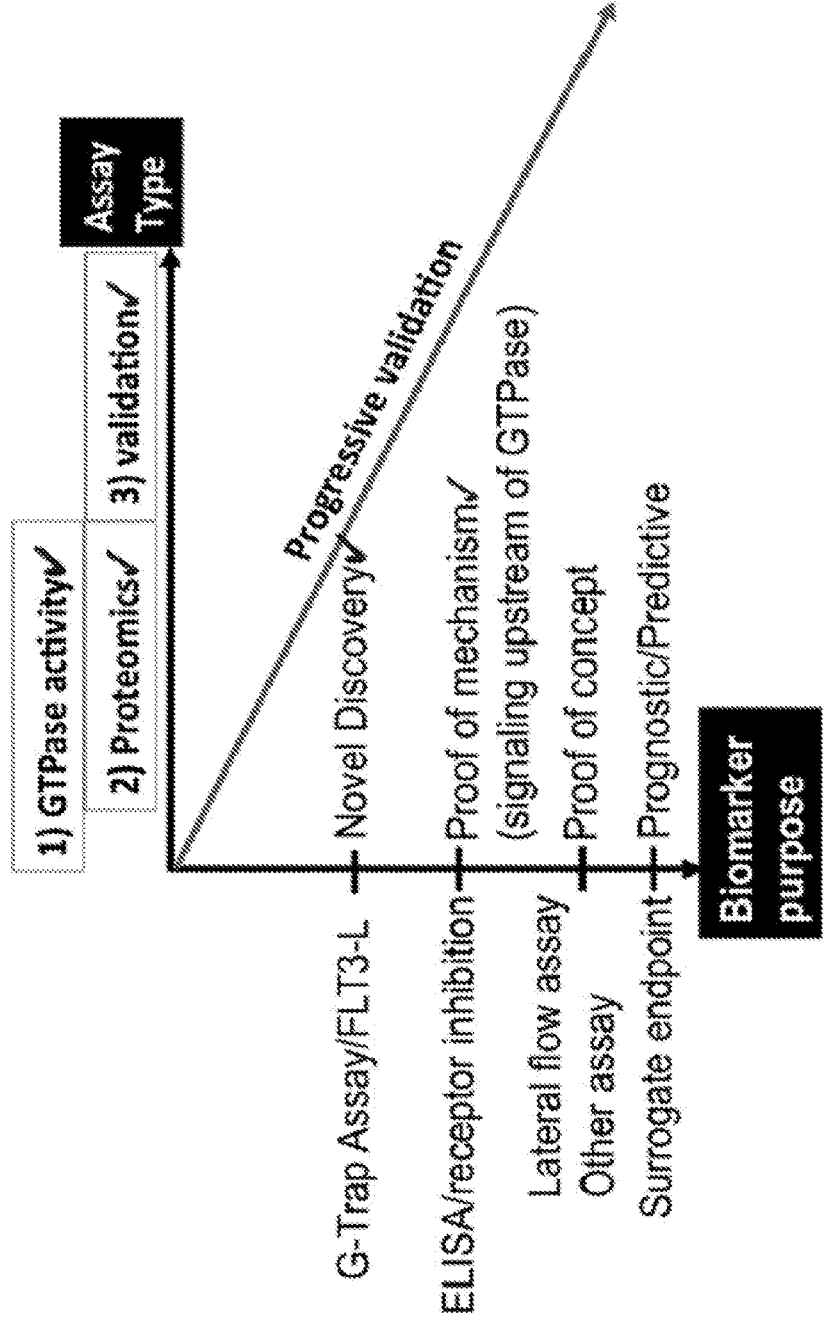
FIG. 11 shows a fit-for-purpose approach to G-Trap assay validation for sepsis diagnosis. The validation approach is an iterative process between discovery and validation, which takes account of both the nature of the technology used and the position of the biomarker in the spectrum between research tool and clinical endpoint. (adapted from ref.[4], second set of references). Check marks represent strong preliminary data from our studies.

In one approach, the inventors take a fit-for-purpose approach (FIG. 10) to develop and validate a minimal viable product. The desired early outcome is a rapid point of care (POC) assay for use in a low resource setting, such as a battlefield setting, nursing home, or rural medical establishment. Preliminary data from longitudinal blood samples of trauma patients showed that it was possible to rapidly (14 samples in <4 hrs; (patient data shown in FIGS. 2-4) and accurately identify patients with early infection before definite clinical diagnosis, based on elevated GTPase activation and increased Flt-3L expression in the plasma of patients. The inventors further showed that the concentration of active GTPases declined in septic patients after appropriate antibiotics were used (Patient 10, 14 and 18 in FIGS. 2-4, 6,7). The inventors have extended the utility of GTPase activity assay as a tool for the discovery of a novel panel biomarkers linked to sepsis in terms: 1) of diagnostic tool discovery; 2) biomarkers that reveal pathophysiological pathways of the disease and thus lead to development of new therapeutic targets. 3) use in monitoring effectiveness of treatment. 4) proxy target indicators of outcomes and guidance for clinical intervention Pilot proteomic studies identified a subset of biomarker candidates correlated to GTPase activity post-infection. Initial tests of biomarker targets confirm a mechanistic connection between the upregulated markers and GTPase activity (FIGS. 6-7).

Figure 5:
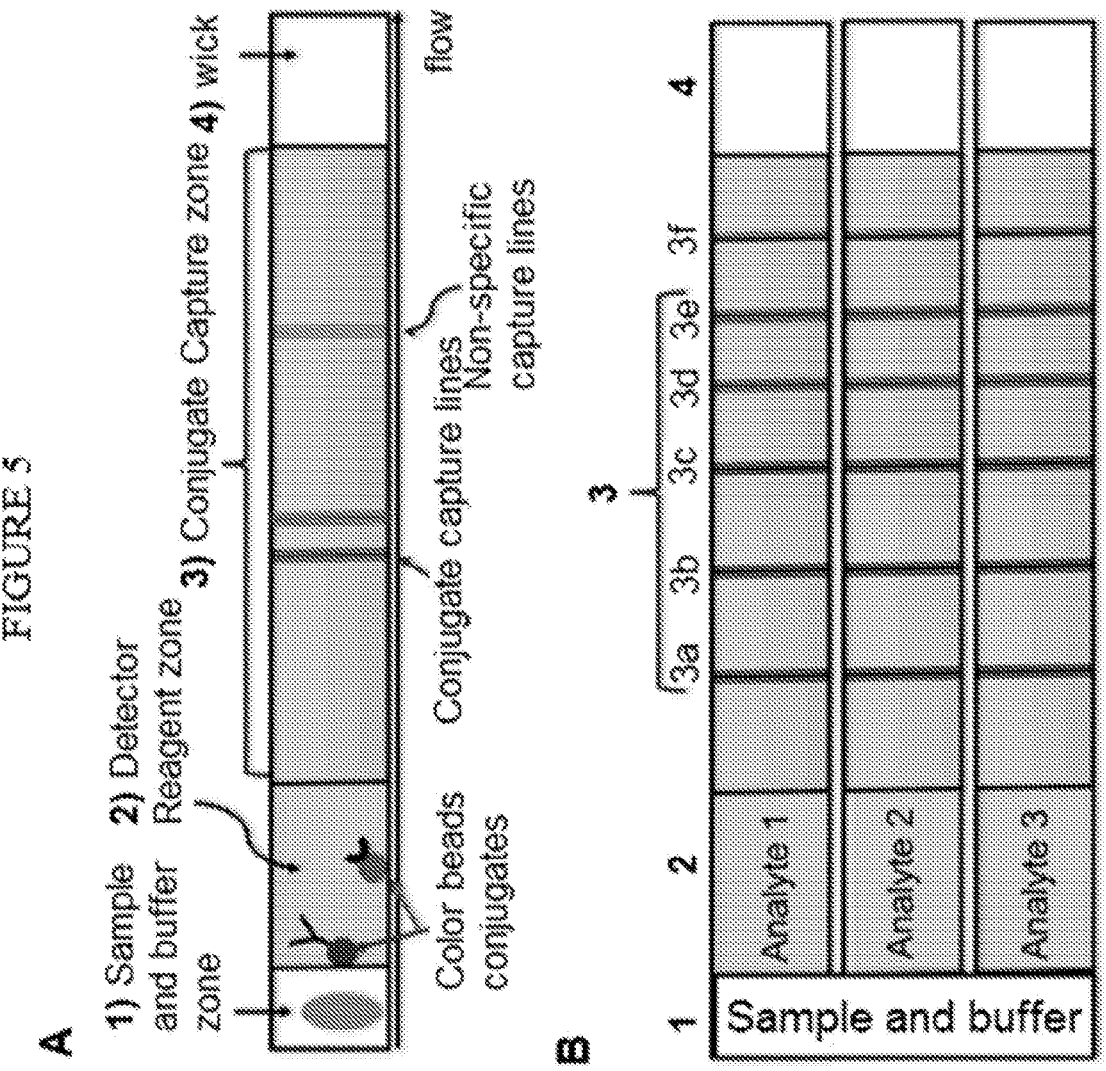
FIG. 5A Lateral flow assay device modules comprise 1) Sample receiving zone, 2) a detector reagent zone, 3 an analyte capture zone, containing a series of immobilized antibodies to capture flowing analytes and 4 a wick matrix to remove excess analyte carrier fluid. B. Multiplex format lateral flow assay device to capture tandem biomarkers such as small Rap1, Rac1 and RhoA small GTPases. Analyte 1-3 might be Effector proteins for Rap1 (Ral GDS-RBD)), Rac1 (PAK-1 RBD) and RhoA (Rhotekin-RBD). Serial antibody capture lines can be used for analyte quantitation based on occupancy patterns of barrier lines established using analytes of known concentration that can be established by flow cytometry. Barrier lines for each branch is functionalized with antibodies for each specific analyte. Note that the principal of immunochromatography used in the depicted assay is the same as the ELISA sandwich method (ELISA can also be used in the present invention, although immunochromatography is preferred at the point-of-care (POC) as a rapid early detection of bacterial infection and sepsis which can be subsequently confirmed (quantitatively) by G-Trap analysis (for Rap1-GTP or Rac1-GTP) and cytokine profile in serial plasma samples (for Flt-3L). Note that blood, plasma, serum, urine and saliva may be used in immunochromatography or ELISA assay. Exemplary immunochromatography assays are well known in the art. See, for example Posthuma-Trumpie, *Anal. Bioanal. Chem.* (2009) 393:569-582.

To translate these results into a useful clinical decision support tool, the inventors propose a proof of concept lateral flow assay design (FIGS. 5A and B) for which commercial kits and organized course instructions for customization to enable detection of specific analytes of interest is available from DCN Diagnostics. In the short term the approach is to exploit the Rap1 and Flt3-L (and optionally Rac1 in addition to the two biomarkers) tandem biomarker as the primary target of the clinical application.

Example Case #1

The results of this patient analysis are presented in FIG. 3. (Patient 18) A 50-year-old male was admitted after being run over by a car. Daily blood draws were obtained with consent for 14 days. The patient developed central line-associated bloodstream infection (CLABSI) and became febrile on day 7/8. Blood cultures drawn from this patient on day 9 were positive for methicillin-sensitive, Gram-positive Staph *Aureus* (MSSA). The patient was treated with appropriate antibiotics. Flt-3L and Rap1 activation showed correlated changes that presaged clinical diagnosis three days later. GTPase and Flt-3L levels began to decline with treatment eventually resulting in resolution of the bacterial infection.

Example Case #2-Patient 10 Tracking the Effectiveness of Antibiotic Treatment

The results of this patient analysis are initially presented in FIG. 4 and fully discussed here with reference to FIG. 6. A 53-year-old male car crash patient had a suspected bacterial infection on day 2 that was confirmed by sputum-culture to be positive for *Haemophilus influenzae* (Gram-negative). Broad-spectrum antibiotics were given and the antibiotic regimen was narrowed on day 7 to 3 days of ceftriaxone (days 7-9) after which antibiotics were stopped. The GTPase assay indicated a failure of treatment on day 9, which was only corrected on day 14. Persistent bacteremia was suggested by an increase in GTP binding to Rap1 (5-fold over baseline) and Rac1 (7-fold over baseline) on day 10, over 3 days before clinical recognition of infection and resumption of antibiotic treatment. Ongoing proteomic studies of serial plasma samples from this patient indicate promising results, such as the GTPase activity correlated increase of inflammatory mediators post day 9. The inventors used proteomics to identify biomarker candidates that are released in these patients' plasma and activate small GTPases. They tested whether the biomarkers 1) reveal the underlying mechanism that underpins GTPase activation; 2) provide a parallel diagnostic readout at infection onset 3) are prognostic or predictive of disease or therapeutic outcome. They envision the expansion of our multiplex biomarker panel to include the discovery proteins causally liked to GTPase activity and sepsis progression.

Pilot study Proteomic of Patient #10 and #14 plasma samples. Laser densitometer readings of duplicate patient plasma samples (#10, and #14) were computer analyzed for differential expression of proteins as previously described [1]. Spot data showing significant differences between patient samples and controls were determined from adjusted p-values using FDR (and Bonferroni) analysis as previously described[1]. Ten spots were selected for mass spectrometry analysis. The selection was based on the magnitude of change in expression as well as positive correlation to trends in GTPase activity. Preliminary validation assay were performed Spot #130-CPN for patient 10 and Spot #102; Angiotensinogen for Patient 14, because of their overt connection to GTPase activity profile and the immediate availability of assay tools to confirm their presence. The value proposition of the invention as a clinical decision support tool is illustrated in FIG. 6. FIG. 6A panels show the patient's vital signs, which are indeterminate. The illness history of Patient 10 is summarized in example Case #2 above caption and recapitulated in FIG. 6B. The G-Trap assay clearly demonstrates how the serial measurement of Rap1-GTP and Rac1-GTP for this patient indicates the worsening condition soon after antibiotics were discontinued, whereas the vital signs do not show significant changes until after the IRB approved study ended on day 14. The subsequent proteomics assay partially revealed the immunological source as anaphylatoxins, which indirectly stimulated the increasing GTPase activity FIG. 6C. The rationale for testing CPN in secondary assays was based on the following. CPN is a metallocarboxypeptidase that regulates complement anaphylatoxins (C3a, C4a, and C5a). [2; 3; 4] For clarity, the expression of carboxypeptidase N (CPN) are superimposed over changes in GTP binding to Rac1 and Rap1 (FIG. 6C) for days 8-11. The changes between GTPase activity and CPN showed positive correlation (Pearson correlation: r 0.98, p<0.01). We reasoned that the plasma upregulation of CPN was due to *Haemophilus influenzae* associated LPS. CPN exerts its proteolytic activity on prochemerin, a zymogen for chemerin a potent chemoattractant ($K_d$~ 0.1 nM) [5] to its receptor ChemR23 (CMKLR1), a GaiPCR for adaptive and innate immune responses recognized by ChemR23 receptor. [6; 7; 8] Chemerin binds. For the purposes of this study, chemerin induces GTP binding to Rap1 and Rac1 downstream of ChemR23.

[5] We used α-NETA an antagonist for ChemR23 ($K_d$~6 µM) to test for the putative presence of CPN activated chemerin in Patient #10's plasma. As shown, in FIG. 6C measurements of Rac1-GTP in cells challenged with patient's plasma on days 2-4 suggests that ChemR23 was not activated, likely due to early antibiotic treatment. However, on day 6 the data show partial sensitivity to α-NETA suggesting an escalation of the inflammatory response likely due to treatment failure. However, with increasing GTPase activity the efficacy of α-NETA diminishes as inhibition of GTPase activity falls from 40% on day 6 to 20% on day 11 and 25% on day 12. This indicates that multiple factors that are yet to be discoverable by proteomics contribute to GTPase activation after day 6.

Patient #14. Patient was hypotensive on admission and his blood pressure monitored continuously (FIG. 7A). Spot #102, identified as angiotensinogen by mass spectrometry, showed an interesting oscillatory pattern that appeared to track the changes in GTP-binding to Rac1 (FIG. 7B) and was correlated to the patient's hypotensive blood pressure. Angiotensinogen is a precursor molecule to angiotensin-II, a ligand for AgtR1 which induces vasoconstriction in a Rac1 dependent pathway. [9; 10] To validate the mass spectrometry result, we used a Renin Assay kit (MAK157 from Sigma) to test for renin, an enzyme secreted by kidneys to promote the production of the protein angiotensin I to mitigate low mean arterial blood pressure associated with the sepsis. [11; 12; 13; 14] As shown in FIG. 7D, the renin activity results were correlated to GTPase activity as welly as the patient's hypotensive pattern. Collectively, our G-Trap assay results were validated by proteomic discovery of angiotensinogen expression, patient blood pressure readings and renin activity assay. In summary, these results demonstrate the utility of the G-Trap assay is a surrogate reporter of infection-specific biomarkers released in the host circulation during early and late stage of infection.

REFERENCES

[1] V. Bondu, R. Schrader, M. A. Gawinowicz, P. McGuire, D. A. Lawrence, B. Hjelle, and T. Buranda, Elevated Cytokines, Thrombin and PAI-1 in Severe HCPS Patients Due to Sin Nombre Virus. Viruses 7 (2015) 559-89.

[2] J. H. Foley, P. F. Cook, and M. E. Nesheim, Kinetics of Activated Thrombin-activatable Fibrinolysis Inhibitor (TAF1a)-catalyzed Cleavage of C-terminal Lysine Residues of Fibrin Degradation Products and Removal of Plasminogen-binding Sites. Journal of Biological Chemistry 286 (2011) 19280-19286.

[3] S. Talens, J. H. G. Lebbink, J. J. M. C. Malfliet, J. A. A. Demmers, S. U. de Willige, F. W. G. Leebeek, and D. C. Rijken, Binding of carboxypeptidase N to fibrinogen and fibrin. Biochemical and biophysical research communications 427 (2012) 421-425.

[4] J. B. Walker, T. M. Binette, M. Mackova, G. R. Lambkin, L. Mitchell, and L. Bajzar, Proteolytic cleavage of carboxypeptidase N markedly increases its antifibrinolytic activity. J Thromb Haemost 6 (2008) 848-55.

[5] O. De Henau, G. N. Degroot, V. Imbault, V. Robert, C. De Poorter, S. McHeik, C. Gales, M. Parmentier, and J. Y. Springael, Signaling Properties of Chemerin Receptors CMKLR1, GPR1 and CCRL2. PloS one 11 (2016) e0164179.

[6] V. Wittamer, J. D. Franssen, M. Vulcano, J. F. Mirjolet, E. Le Poul, I. Migeotte, S. Brezillon, R. Tyldesley, C. Blanpain, M. Detheux, A. Mantovani, S. Sozzani, G. Vassart, M. Parmentier, and D. Communi, Specific recruitment of antigen-presenting cells by chemerin, a novel processed ligand from human inflammatory fluids. The Journal of experimental medicine 198 (2003) 977-85.

[7] W. Vermi, E. Riboldi, V. Wittamer, F. Gentili, W. Luini, S. Marrelli, A. Vecchi, J. D. Franssen, D. Communi, L. Massardi, M. Sironi, A. Mantovani, M. Parmentier, F. Facchetti, and S. Sozzani, Role of ChemR23 in directing the migration of myeloid and plasmacytoid dendritic cells to lymphoid organs and inflamed skin. The Journal of experimental medicine 201 (2005) 509-15.

[8] J. Kaur, R. Adya, B. K. Tan, J. Chen, and H. S. Randeva, Identification of chemerin receptor (ChemR23) in human endothelial cells: chemerin-induced endothelial angiogenesis. Biochemical and biophysical research communications 391 (2010) 1762-8.

[9] G. Loirand, and P. Pacaud, Involvement of Rho GTPases and their regulators in the pathogenesis of hypertension. Small GTPases 5 (2014) 1-10.

[10] G. Loirand, and P. Pacaud, Involvement of Rho GTPases and their regulators in the pathogenesis of hypertension. Small GTPases 5 (2014).

[11] N. J. Brown, M. Agirbasli, and D. E. Vaughan, Comparative effect of angiotensin-converting enzyme inhibition and angiotensin II type 1 receptor antagonism on plasma fibrinolytic balance in humans. Hypertension 34 (1999) 285-90.

[12] A. Dendorfer, W. Raasch, K. Tempel, and P. Dominiak, Comparison of the vascular and antiadrenergic activities of four angiotensin II type 1 antagonists in the pithed rat. Journal of hypertension 20 (2002) 1151-6.

[13] R. M. Edwards, N. Aiyar, E. H. Ohlstein, E. F. Weidley, E. Griffin, M. Ezekiel, R. M. Keenan, R. R. Ruffolo, and J. Weinstock, Pharmacological characterization of the nonpeptide angiotensin II receptor antagonist, SK&F 108566. J Pharmacol Exp Ther 260 (1992) 175-81.

[14] R. M. Edwards, E. J. Stack, E. F. Weidley, N. Aiyar, R. M. Keenan, D. T. Hill, and J. Weinstock, Characterization of renal angiotensin II receptors using subtype selective antagonists. J Pharmacol Exp Ther 260 (1992) 933-8.

Example

Development of a blood test. The development of a blood test for infection based on the level of Flt-3L in plasma and small GTPase activation in WBC isolated from patient blood draws. The inventors have shown that in vivo GTPase activity in white blood cells (WBC) of infected patients is elevated relative to uninfected patients in response to circulating bacterial and host response factors. Inasmuch as GTPase activity is central to the chemotactic motility of active white blood cells, which are mobilized post-infection,[14,15] the current strategy has the practical advantage of basing the assay on a traditional blood test.

Research Design 1. Study Samples. a) Collection of residual peripheral blood test samples (healthy, preseptic, septic, and post-septic patients) after standard of care (SOC) testing at TriCore under UNM IRB #18-068. b) Consultation with Biostatistics Core at the UNM Clinical & Translational Science Center (CTSC) on all aspects of study design, biostatistics, and basic data management of our study.

G-Trap Assay

A G-Trap assay is used to measure active GTPases in culture positive WBC, culture negative WBC or healthy control and endothelial cells exposed to culture positive patient plasma samples as a positive control (FIGS. 8 and 9). a) WBC and plasma are separated from whole blood. b) WBC are lysed and quantitatively analyzed with G-Trap beads.[9] c) Plasma aliquots selected and analyzed for cytokine expression (The workflow is summarized in (FIG. 10). d) Plasma aliquots selected for challenging quiescent endothelial and WBC, cells are lysed and analyzed by G-Trap. In vivo GTP activity in WBC is compared to activity in quiescent WBC activated with plasma of septic patients. e) To assess the accuracy of the G-Trap assay, quantification of the proportion of blood culture-positive samples that are determined positive by G-Trap testing. Positive G-Trap is defined as ≥ a 2-fold increase in GTP binding above baseline. f) Based on our preliminary data; Gram-positive infections elicit lower GTP binding compared to Gram-negative infections. We will seek to determine whether this difference is statistically significant among sepsis patients.

G-Trap Validation Phase: a) Test for agreement between G-Trap and blinded blood culture tests. A two-way comparison between the G-Trap and blood culture, and clinical diagnosis will be performed as described in section 9 of Clinical and Laboratory Standards Institute Guideline EP12-A.[16] b) Test for assay robustness by spiking biological samples with titers of Flt-3L. Establish a signal to noise ratio (SNR), limits of detection (LOD), and the dynamic ranges (ratio of the maximum and minimum concentrations over which fluorescence signal can be recorded)

Development of Point of Care Lateral Flow Assay for tandem measurement of Rac1-GTP and Flt-3L a) Adapt Lateral Flow Assay kits from DCN for analysis of Rac1-GTP and Alt-3L. b) G-Trap multiplex beads are functionalized with RalGDS, which specifically binds to Rac1-GTP and characterized for the flow cytometry format, to test the translation of the flow cytometry assay to POC format. With further system development, establish the assay for Flt-3L and validate performance as described for the flow cytometry assay.

Identification of molecular determinants of small GTPase activation present in the plasma of bacteria infected patients. The inventors have shown that bacterial infection stimulates the release of novel infection biomarkers that are causally linked to GTPase activity, in particular Rap1-GTP, as well as Flt3-L.

The approach taken pursuant to the present invention is based on the development of an understanding of the role of host response to infection. Flt-3L is a cytokine that stimulates the expansion of antigen-presenting dendritic cells and stimulates signaling upstream of the small GTPase Rap1, an effector of integrin inside-out signaling, crucial for leukocyte adhesion. Thus, the first step is in establishing a point of care (POC) platform based on tandem measurement of Flt-3L and Rap1-GTP as a clinical tool for early infection diagnosis, through minimally invasive blood sample testing. Results from the proteomic study produce novel biomarkers that are causally linked to GTPase activity. Thus, improvement to the diagnostic precision occurs by expanding the sepsis panel through multiplexing.

Military Applications: To improve the quality of healthcare delivery to all beneficiaries of medicine in the military, the DOD developed the Military Acuity Model (MAM).[18] The MAM enables healthcare workers to track multiple health data points and to assign a numeric score for each patient. This score helps healthcare providers, to identify higher-risk patients and to improve outcomes. Baseline readings of assay targets could provide baseline readings, against which a future diagnosis of infection can be made. Infections related to burn injuries are common to all modern military conflicts. The transit of medical evacuees from overseas battle-fields involves transportation of several days through various medical facilities with differing levels of capabilities.[19] Monitoring the activation status of the patient's blood leukocytes as a routine of patient care allows the capture of the onset of infection in trauma patients and the efficacy of antibiotic treatment. Military personnel go to places where the pathogens may not be well known, or they may be targets of weaponized organic matter, so it would be difficult to diagnose by traditional methods. The G-Trap assay measures an immune response to the presence of pathogens and would provide an appropriate early warning system.

REFERENCES (FIRST SET OF REFERENCES)

1. Stearns-Kurosawa, D. J., Osuchowski, M. F., Valentine, C., Kurosawa, S. & Remick, D. G. The Pathogenesis of Sepsis. *Annu Rev Pathol*-Mech 6, 19-48 (2011).
2. Skibsted, S. et al. Biomarkers of endothelial cell activation in early sepsis. *Shock* 39, 427-432 (2013).
3. Kim, W. S. & Lee, H. J. Management of sepsis. *J Korean Med Assoc* 56, 819-826 (2013).
4. Hernandez, G., Bruhn, A. & Ince, C. Microcirculation in Sepsis: New Perspectives. *Current vascular pharmacology* 11, 161-169 (2013).
5. McAdow, M. et al. Preventing *Staphylococcus aureus* Sepsis through the Inhibition of Its Agglutination in Blood. *PLoS pathogens* 7 (2011).
6. Sun, H. M. The interaction between pathogens and the host coagulation system. *Physiology* 21, 281-288 (2006)
7. van der Poll, T. & Herwald, H. The coagulation system and its function in early immune defense. *Thrombosis and haemostasis* 112 (2014).
8. Wang, H. J. et al. Identification of four novel serum protein biomarkers in sepsis patients encoded by target genes of sepsis-related miRNAs. *Clin Sci* 126, 857-867 (2014).
9. Sankar, V. & Webster, N. R. Clinical application of sepsis biomarkers. *J Anesth* 27, 269-283 (2013).
10. Pierrakos, C. & Vincent, J. L. Sepsis biomarkers: a review, *Critical care* 14 (2010).
11. Faix, J. D. Established and novel biomarkers of sepsis. *Biomark Med* 5, 117-130 (2011).
12. Charles, P. E. & Gibot, S. Predicting outcome in patients with sepsis: new biomarkers for old expectations. *Critical care* 18 (2014).
13. Mihajlovic, D., Brkic, S., Uvelin, A., Draskovic, B. & Vrsajkov, V. Use of presepsin and procalcitonin for prediction of SeptiFast results in critically ill patients. *J Crit Care* 40, 197-201 (2017).
14. Geissmann, F. et al. Development of monocytes, macrophages, and dendritic cells. *Science* (New York, N. Y 327, 656-661 (2010).
15. Randolph, G. J., Angeli, V. & Swartz, M. A. Dendritic-cell trafficking to lymph nodes through lymphatic vessels. *Nat Rev Immunol* 5, 617-628 (2005).
16. Shortman, K. & Naik, S. H. Steady-state and inflammatory dendritic-cell development. *Nat Rev Immunol* 7, 19-30 (2007).
17. Steinman, R. M. & Banchereau, J. Taking dendritic cells into medicine. *Nature* 449, 419-426 (2007).
18. Schmidt, A., Caron, E. & Hall, A. Lipopolysaccharide-induced activation of beta2-integrin function in macrophages requires Irak kinase activity, p38 mitogen-activated protein kinase, and the Rap1 GTPase. *Molecular and cellular biology* 21, 438-448 (2001).

19. Ring, S. et al. Regulatory T cell-derived adenosine induces dendritic cell migration through the Epac-Rap1 pathway. *J Immunol* 194, 3735-3744 (2015).
20. Lagarrigue, F., Kim, C. & Ginsberg, M. H. The Rap1-RIAM-talin axis of integrin activation and blood cell function. *Blood* 128, 479-487 (2016).
21. Reinhart, K., Bauer, M., Riedemann, N. C. & Hartog, C. S. New Approaches to Sepsis: Molecular Diagnostics and Biomarkers. *Clin Microbiol Rev* 25, 609-634 (2012).
22. Lvovschi, V. et al. Cytokine profiles in sepsis have limited relevance for stratifying patients in the emergency department: a prospective observational study. *PloS one* 6, e28870 (2011).
23. Buranda, T. et al. Rapid parallel flow cytometry assays of active GTPases using effector beads. *Analytical biochemistry* 144, 149-157 (2013).
24. Worbs, T., Hammerschmidt, S. I. & Forster, R. Dendritic cell migration in health and disease. *Nat Rev Immunol* 17, 30-48 (2017).
25. van der Poll, T., van de Veerdonk, F. L., Scicluna, B. P. & Netea, M. G. The immunopathology of sepsis and potential therapeutic targets. *Nat Rev Immunol* (2017).

ADDITIONAL REFERENCES (SECOND SET OF REFERENCES)

1. Levy M M, Gesten F C, Phillips G S, et al. Mortality Changes Associated with Mandated Public Reporting for Sepsis. The Results of the New York State Initiative. *Am J Respir Crit Care Med.* 2018; 198:1406-12.
2. Meyer N, Harhay M O, Small D S, et al. Temporal Trends in Incidence, Sepsis-Related Mortality, and Hospital-Based Acute Care After Sepsis. *Crit Care Med.* 2018; 46:354-60.
3. Prescott H C, Kepreos K M, Wiitala W L and Iwashyna T J. Temporal Changes in the Influence of Hospitals and Regional Healthcare Networks on Severe Sepsis Mortality. *Crit Care Med.* 2015; 43:1368-74.
4. Cummings J, Raynaud F, Jones L, Sugar R and Dive C. Fit-for-purpose biomarker method validation for application in clinical trials of anticancer drugs. *Br J Cancer.* 2010; 103:1313-7.
5. Wang H J, Wang B Z, Zhang P J, et al. Identification of four novel serum protein biomarkers in sepsis patients encoded by target genes of sepsis-related miRNAs. *Clinical Science.* 2014; 126:857-67.
6. Sankar V and Webster N R. Clinical application of sepsis biomarkers. *Journal of Anesthesia.* 2013; 27:269-83.
7. Cherfils J and Zeghouf M. Regulation of small GTPases by GEFs, GAPs, and GDIs. *Physiol Rev.* 2013; 93:269-309.
8. Lemichez E and Aktories K. Hijacking of Rho GTPases during bacterial infection. *Exp Cell Res.* 2013; 319:2329-36.
9. Simons P C, Bondu V, Wandinger-Ness A and Buranda T. Small volume Flow Cytometry-Based Multiplex Analysis of the Activity of Small GTPases *Methods Mol. Biol.* 2018; 1821:177-195.
10. Schmidt A, Caron E and Hall A. Lipopolysaccharide-induced activation of beta2-integrin function in macrophages requires Irak kinase activity, p38 mitogen-activated protein kinase, and the Rap1 GTPase. *Mol Cell Biol.* 2001; 21:438-48.
11. Worbs T, Hammerschmidt S I and Forster R. Dendritic cell migration in health and disease. *Nat Rev Immunol.* 2017; 17:30-48.
12. Ring S, Pushkarevskaya A, Schild H, et al. Regulatory T cell-derived adenosine induces dendritic cell migration through the Epac-Rap1 pathway. *J Immunol.* 2015; 194:3735-44.
13. Lagarrigue F, Kim C and Ginsberg M H. The Rap1-RIAM-talin axis of integrin activation and blood cell function. *Blood.* 2016; 128:479-87.
14. Fan Z, McArdle S, Marki A, et al. Neutrophil recruitment limited by high-affinity bent beta2 integrin binding ligand in cis. *Nat Commun.* 2016; 7:12658.
15. Diabate M, Munro P, Garcia E, et al. *Escherichia coli* alpha-hemolysin counteracts the anti-virulence innate immune response triggered by the Rho GTPase activating toxin CNF1 during bacteremia. *PLOS Pathog.* 2015; 11: e1004732.
16. Clark L W, P. E. G, R M and K. L. M. User Protocol for Evaluation of Qualitative Test Performance; Approved Guideline EP12-A. CLSI.http://www.clsi.org/source/orders/free/ep12-a2.pdf 2002.
17. Bondu V, Schrader R, Gawinowicz M A, et al. Elevated Cytokines, Thrombin and PAI-1 in Severe HCPS Patients Due to Sin Nombre Virus. *Viruses.* 2015; 7:559-89.
18. Howard D. Using the Military Medical Acuity Model to guide patient care. *Nursing.* 2016, 40:147.
19. D'Avignon L C, Chung K K, Saffle J R, Renz E M, Cancio L C and Prevention of Combat-Related Infections Guidelines P. Prevention of infections associated with combat-related burn injuries. *J Trauma* 2011; 71: S282-9.

The invention claimed is:

1. A method of treating a patient suspected of having a microbial infection which is causing sepsis or which is likely to cause sepsis in the patient, the method comprising:
   obtaining a biological sample from said patient;
   measuring the expression levels of Ras-related protein 1 guanosine triphosphatase (Rap1-GTP) and Fms-related tyrosine kinase ligand (Flt3-L) biomarkers in said sample;
   comparing the expression levels of Rap1-GTP and Flt3-L in said biological sample with a control or standard obtained from a healthy patient, wherein an elevated expression level of Rap1-GTP and Flt3L compared to the control or standard evidences that the patient has a microbial infection in an early stage of sepsis or which is likely to cause sepsis in said patient; and
   treating said patient for said microbial infection with an effective amount at least one antibiotic alone or in combination with an antimicrobial agent.

2. The method according to claim 1 wherein said patient is treated with a broad-spectrum antibiotic.

3. The method according to claim 1 wherein said patient is treated with a broad-spectrum antibiotic in combination with an additional antimicrobial agent.

4. The method according to claim 1 wherein an expression level of Ras-related C3 botulinum toxin substrate 1 guanosine triphosphatase (Rac1-GTP) biomarker in said sample is also measured and compared with a control or standard, such that the expression level of Rac1-GTP in said sample compared to said control or standard further evidences that the patient has a microbial infection in an early stage of sepsis or which is likely to cause sepsis in said patient.

5. The method according to claim 1 wherein said biological sample from said patient is a whole blood sample, a plasma sample, a serum sample, a white blood cell sample, a cell lysate sample derived from the patient's leukocytes or a mixture thereof.

6. The method according to claim 4 wherein said sample is a serum sample or a cell lysate sample derived from the patient's leukocytes.

7. The method according to claim 1 wherein said biological sample from said patient is a cell lysate derived from the patient's leukocytes or a mixture thereof.

8. The method according to claim 1 wherein the expression levels of Rap1-GTP and FLT-3L are each at least 1.5 times the expression levels of Rap1-GTP and FLT-3L of the control or standard.

9. The method according to claim 1 wherein the expression levels of Rap1-GTP and FLT-3L are two times to fifteen times the expression levels of Rap1-GTP and FLT-3L of the control or standard.

10. The method according to claim 1 wherein the expression levels of Rap1-GTP and FLT-3L are two times to ten times the expression levels of Rap1-GTP and FLT-3L of the control or standard.

11. The method according to claim 10 wherein the expression level of Rac1-GTP is at least 1.5 times the expression level of Rac1-GTP of the control or standard.

12. A method of treating a patient who has a microbial infection which is causing sepsis or which is likely to cause sepsis in the patient, the method comprising:
obtaining a biological sample from said patient;
measuring the expression levels of Ras-related protein 1 guanosine triphosphatase (Rap1-GTP), Fms-related tyrosine kinase ligand (Flt3-L) and Ras-related C3 botulinum toxin substrate 1 guanosine triphosphatase (Rac1-GTP) biomarkers in said sample;
comparing the expression levels of Rap1-GTP, Flt3-L and Rac1-GTP biomarkers in said biological sample with a control or standard obtained from a healthy patient, wherein an elevated expression level of Rap1-GTP, Flt3L and Rac1-GTP compared to the control or standard evidences that the patient has a microbial infection in an early stage of sepsis or which is likely to cause sepsis in said patient; and
treating said patient for said microbial infection with an effective amount at least one antibiotic alone or in combination with an antimicrobial agent.

13. A lateral flow assay comprising:
i) at least one sample and buffer zone where a sample is to be introduced onto the assay;
ii) a detector reagent or primary capture zone comprising detector reagents where Flt3-L and Rap1-GTP analytes become bound to said detector reagents, wherein said detector reagents for Flt3-L comprise reporter Flt3-L antibodies and detector reagents for Rap1-GTP are selected from the group consisting of reporter Rap1-GTP antibodies and RalGDS-RBD reporter protein, said detector reagents being specific to said Flt3-L and Rap1-GTP analytes respectively and wherein each analyte specific antibody or protein is conjugated to a reporter to provide a Flt3-L antibody conjugate or a Rap1-GTP antibody or protein reporter conjugate after binding, wherein each of said analyte bound antibody or protein reporter conjugate is capable of flowing through said assay;
iii) an analyte capture zone comprising analyte capture lines for Flt3-L and Rap1-GTP each of which capture lines comprises a support which is conjugated to a capture reagent comprising a capture antibody which is specific for binding said Flt3-L antibody conjugate or said Rap1-GTP antibody or protein reporter conjugate and wherein said Flt3-L antibody conjugate or said Rap1-GTP antibody or protein reporter conjugate becomes concentrated after binding to said capture reagent at said capture lines; and
iv) a terminal wick zone which allows wicking of solution which has flowed through the assay to its terminal zone.

14. The assay of claim 13 wherein said biological sample is whole blood, serum, plasma, white blood cells taken from said patient or a cell lysate sample derived from patient leukocytes.

15. The assay of claim 13 wherein said biological sample is serum or a cell lysate sample derived from patient leukocytes.

16. The assay of claim 14 wherein said reporter is a colored readout bead, a quantum dot or colloidal gold.

17. The assay of claim 14 wherein said reporter is a colored readout bead or quantum dot.

18. The assay of claim 17 wherein said report is a colored readout bead.

19. The assay of claim 14 wherein said Flt3-L detector reagent is an anti-Flt3-L antibody and said Rap1-GTP detector reagent is an anti-Rap1-GTP antibody.

20. The assay of claim 18 wherein at least one of said antibodies is a monoclonal antibody.

21. The assay according to claim 14 wherein said detector reagent for Rap1-GTP is RalGDS-RBD and said Rap1-GTP reporter conjugate is GST RalGDS-RBD fusion protein.

22. The assay according to claim 14 wherein said capture lines for Flt3L comprise supported antibodies capable of binding Flt3-L detector reagents and said capture lines for Rap1-GTP comprise supported antibodies capable of binding Rap1-GTP detector reagents.

23. The assay according to claim 14 further comprising non-specific IgG antibodies and/or non-specific GST fusion proteins to establish and/or increase specificity of the assay.

24. A multiplex lateral flow assay comprising:
i) a lateral flow cassette with two or three lanes for determining the concentration of analytes in a biological sample obtained from a patient wherein said analytes comprise Flt-3L and Rap1-GTP, and optionally Rac1-GTP;
ii) a sample and buffer zone in each lane where a sample is to be introduced onto the assay;
iii) a detector or primary capture zone in each lane where Flt3-L, Rap1-GTP and optionally Rac1-GTP analytes become bound to detector reagents wherein said detector reagents are analyte specific for each of said analytes, wherein said detector reagents for Flt3-L comprise anti-Flt3-L antibodies, said detector reagents for Rap1-GTP comprise anti-Rap1-GTP antibodies or RalGDS-RBD protein and said detector reagents for Rac1-GTP comprise anti-Rac1-GTP antibodies or PAK-1RBD protein and wherein each detector reagent is conjugated to a reporter and each of said detector reagents is capable of flowing through said lane of said assay after binding said analyte;
iv) an analyte capture zone comprising analyte capture lines for Flt3-L, Rap1-GTP and optionally Rac1-GTP, each of which capture lines comprises a support which is conjugated to a capture reagent comprising a capture antibody which is specific for binding said FTL3L detector reagent, a capture antibody which is specific for binding said Rap1-GTP detector reagent and optionally, a capture antibody which is specific for binding said Rac1-GTP detector reagent and wherein said FLT3-L detector reagent, said Rap1-GTP detector reagent and said optional Rac1-GTP detector reagent becomes concentrated at said capture line after binding to said capture reagent; and v) a terminal wick zone which allows wicking of solution which has flowed through the assay to its terminal zone.

25. The multiplex lateral flow assay according to claim 24 wherein said assay comprises in said detector reagent or capture zone a Rac1-GTP detector reagent comprising anti-Rac1-GTP antibodies or a protein comprising PAK-1RBD which are specific for Rac1-GTP and which are conjugated to a reporter to provide a reporter Rac1-GTP antibody conjugate or a reporter GST PAK-1 RBD reporter conjugate after binding which is capable of flowing through said assay, and in said capture zone an analyte capture line specific for Rac1-GTP comprising a support which is conjugated to a capture reagent comprising a capture antibody which is specific for binding said Rac1-GTP detector reagent and wherein said Rac1-GTP detector reagent becomes concentrated in said capture line after binding to said Rac1-GTP capture reagent at said Rac1-GTP capture line.

26. The assay according to claim 24 wherein said reporter is colloidal gold, a colored readout bead or quantum dot.

27. The assay of claim 24 wherein said biological sample is whole blood, serum, plasma, white blood cells taken from said patient or a cell lysate sample derived from patient leukocytes.

28. The assay of claim 24 wherein said biological sample is serum or a cell lysate sample derived from patient leukocytes.

29. The assay of claim 24 wherein said reporter is a colored readout bead.

30. The assay of claim 24 wherein said Flt3-L detector reagent is an anti-Flt3-L antibody, said Rap1-GTP detector reagent is an anti-Rap1-GTP antibody and said optional Rac1-GTP detector reagent is an anti-Rac1-GTP antibody.

31. The assay of claim 30 wherein at least one of said antibodies is a monoclonal antibody.

32. The assay according to claim 24 wherein said detector reagent for Rap1-GTP is RalGDS-RBD and said Rap1-GTP reporter conjugate is GST RalGDS-RBD fusion protein and said optional detector reagent for Rac1-GTP is PAK-1RBD and said Rac1-GTP reporter conjugate is GST PAK-1 RBD.

33. A lateral flow assay kit comprising:
   i. A lateral flow cassette with single or multiple lanes for determining user specified analytes Flt3-L, Rap1-GTP and optionally, Rac1-GTP;
   ii. Bioconjugate detector reagent reporters for each of the analytes to be measured comprising reporters functionalized with detector reagent antibodies for Flt3-L, detector reagent antibodies or RalGDS-RBD protein for Rap1-GTP and optional detector reagent antibodies or PAK-1 RBD for Rac1-GTP, wherein said reporters are colored readout beads for qualitative analysis or quantum dots or colloidal gel for fluorescence readout quantitative analysis;
   iii. A detector or primary capture zone in each lane where Flt3-L, Rap1-GTP and optional Rac1-GTP analytes become bound to said bioconjugate detector reagents;
   iv. An analyte capture zone comprising analyte capture lines for Flt3-L, Rap1-GTP and optionally Rac1-GTP, each of which capture lines comprises a support which is conjugated to a capture reagent comprising a capture antibody which is specific for binding said FTL3L detector reagent, a capture antibody which is specific for binding said Rap1-GTP detector reagent and optionally, a capture antibody which is specific for binding said Rac1-GTP detector reagent and wherein said FLT3-L detector reagent, said Rap1-GTP detector reagent and said optional Rac1-GTP detector reagent becomes concentrated at said capture line after binding to said capture reagent;
   v. Working Buffer reagents;
   vi. Instructions for using the assay; and
   vii. A graph setting forth standards for correlating an observed pattern of analyte concentration captured at said analyte capture lines of said lateral flow cassettes in the test sample to analyte concentration in the standard.

34. The kit according to claim 33 wherein said reporters comprise colored readout beads for qualitative analysis or quantum dots for quantitative analysis.

35. The kit according to claim 33 wherein said bioconjugate reporters for each of the analytes to be measured comprise reporters functionalized with antibodies for Flt3-L, antibodies or RalGDS-RBD protein for Rap1-GTP and antibodies or PAK-1 RBD for Rac1-GTP.

* * * * *